US011220523B2

(12) United States Patent
Ernst et al.

(10) Patent No.: US 11,220,523 B2
(45) Date of Patent: Jan. 11, 2022

(54) CARBOHYDRATE LIGANDS THAT BIND TO IGM ANTIBODIES AGAINST MYELIN-ASSOCIATED GLYCOPROTEIN

(71) Applicant: UNIVERSITÄT BASEL, Basel (CH)

(72) Inventors: Beat Ernst, Magden (CH); Ruben Herrendorff, Basel (CH); Andreas Steck, Epalinges (CH); Fan Yang, Basel (CH)

(73) Assignee: UNIVERSITÄT BASEL, Basel (CH)

( * ) Notice: Subject to any disclaimer, the term of this patent is extended or adjusted under 35 U.S.C. 154(b) by 0 days.

(21) Appl. No.: 16/848,268

(22) Filed: Apr. 14, 2020

(65) Prior Publication Data

US 2021/0061838 A1 Mar. 4, 2021

Related U.S. Application Data

(63) Continuation of application No. 15/977,422, filed on May 11, 2018, now Pat. No. 10,662,212, which is a continuation of application No. 15/124,913, filed as application No. PCT/EP2015/055140 on Mar. 12, 2015, now Pat. No. 9,994,605.

(30) Foreign Application Priority Data

Mar. 13, 2014 (EP) .................................... 14159528

(51) Int. Cl.

| | |
|---|---|
| ***C07H 15/203*** | (2006.01) |
| ***C07H 15/207*** | (2006.01) |
| ***C08G 69/10*** | (2006.01) |
| ***C08G 69/48*** | (2006.01) |
| ***G01N 33/68*** | (2006.01) |
| ***C08F 2/00*** | (2006.01) |
| ***C08F 120/36*** | (2006.01) |

(52) U.S. Cl.

CPC ......... *C07H 15/207* (2013.01); *C07H 15/203* (2013.01); *C08F 2/00* (2013.01); *C08F 120/36* (2013.01); *C08G 69/10* (2013.01); *C08G 69/48* (2013.01); *G01N 33/6896* (2013.01); *G01N 2400/02* (2013.01); *G01N 2800/285* (2013.01)

(58) Field of Classification Search

None

See application file for complete search history.

(56) References Cited

U.S. PATENT DOCUMENTS

| | | | |
|---|---|---|---|
| 5,155,004 | A | 10/1992 | Kojima |
| 5,470,843 | A | 11/1995 | Stahl et al. |
| 5,695,759 | A | 12/1997 | Good et al. |
| 5,846,951 | A | 12/1998 | Gregoriadis |
| 5,874,411 | A | 2/1999 | Srivastava et al. |
| 5,977,080 | A | 11/1999 | Rosen et al. |
| 5,985,578 | A | 11/1999 | Pestronk |
| 6,020,140 | A | 2/2000 | Pestronk |
| 6,037,467 | A | 3/2000 | Stahl et al. |
| 6,077,681 | A | 6/2000 | Pestronk |
| 6,114,388 | A | 9/2000 | Geffard |
| 6,399,071 | B1 | 6/2002 | Duthaler et al. |
| 6,399,578 | B1 | 6/2002 | Jack et al. |
| 6,491,922 | B1 | 12/2002 | Ho |
| 6,994,970 | B1 | 2/2006 | Ronspeck et al. |
| 7,205,382 | B2 | 4/2007 | Ronspeck et al. |
| 7,294,615 | B1 | 11/2007 | Bovin et al. |
| 7,612,183 | B2 | 11/2009 | Ellis et al. |
| 8,071,731 | B2 | 12/2011 | Ellis et al. |

(Continued)

FOREIGN PATENT DOCUMENTS

| | | | |
|---|---|---|---|
| CA | 2 332 571 | A1 | 1/2000 |
| CN | 101123990 | A | 2/2008 |

(Continued)

OTHER PUBLICATIONS

Ariga et al., "Characterization of Sulfated Glucuronic Acid Containing Glycolipids Reacting with IgM M-proteins in Patients with Neuropathy," Journal of Biological Chemistry 262(2), Jan. 15, 1987, pp. 848-853.

Ariga, T., "The role of sulfoglucuronosyl glycosphingolipids in the pathogenesis of monoclonal IgM paraproteinemia and peripheral neuropathy," Proc Jpn Acad Ser B Phys Biol Sci, vol. 87, Jul. 2011, pp. 386-404.

Burger, D et al., "Identification of the glycosylated sequons of human myelin-associated glycoprotein," Biochem Biophys Res Commun, vol. 197, Iss. 2, Dec. 15, 1993, pp. 457-464.

(Continued)

*Primary Examiner* — Traviss C McIntosh, III

(74) *Attorney, Agent, or Firm* — Fenwick & West LLP

(57) ABSTRACT

The invention relates to carbohydrate ligands presenting the minimal Human Natural Killer-1 (HNK-1) epitope that bind to anti-MAG (myelin-associated glycoprotein) IgM antibodies, and their use in diagnosis as well as for the treatment of anti-MAG neuropathy. In particular, the invention relates to disaccharides of formula (I) and (II) wherein Z is optionally substituted phenyl, heteroaryl, arylcarbonyl, or heteroarylmethyl, and to therapeutically acceptable polymers comprising a multitude of substituents of formula (I) and/or formula (II), wherein Z is a bifunctional linker connecting the disaccharides to the polymer backbone.

(I)

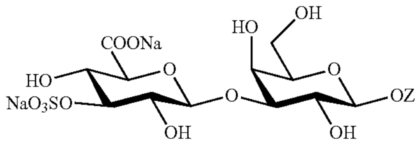

(II)

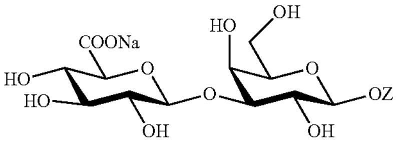

11 Claims, 3 Drawing Sheets

(56) References Cited

U.S. PATENT DOCUMENTS

| | | | |
|---|---|---|---|
| 8,420,593 | B1 | 4/2013 | Miller |
| 9,719,987 | B2 | 8/2017 | Mañez Mendiluce |
| 9,994,605 | B2 | 6/2018 | Ernst et al. |
| 2002/0164347 | A1 | 11/2002 | Duthaler et al. |
| 2002/0177161 | A1 | 11/2002 | Latov et al. |
| 2003/0049692 | A1 | 3/2003 | Latov et al. |
| 2004/0038311 | A1 | 2/2004 | Pestronk |
| 2004/0043431 | A1 | 3/2004 | Vojdani |
| 2004/0087765 | A1 | 5/2004 | Ronspeck et al. |
| 2004/0156840 | A1 | 8/2004 | Witte et al. |
| 2006/0165681 | A1 | 7/2006 | Ellis et al. |
| 2006/0280685 | A1 | 12/2006 | Popko et al. |
| 2007/0244038 | A1 | 10/2007 | Varki et al. |
| 2008/0220988 | A1 | 9/2008 | Zhou |
| 2009/0155292 | A1 | 6/2009 | Santamaria et al. |
| 2009/0169636 | A1 | 7/2009 | O'Hagan et al. |
| 2009/0258792 | A1 | 10/2009 | Wang et al. |
| 2011/0085981 | A1 | 4/2011 | Wang |
| 2012/0039984 | A1 | 2/2012 | Boons et al. |
| 2015/0283247 | A1 | 10/2015 | Auzely-Velty et al. |

FOREIGN PATENT DOCUMENTS

| | | | |
|---|---|---|---|
| CN | 101863930 | A | 10/2010 |
| CN | 101917985 | A | 12/2010 |
| CN | 103108654 | A | 5/2013 |
| CN | 104661684 | A | 5/2015 |
| DE | 195 26 675 | A1 | 3/1996 |
| DE | 199 30 177 | A1 | 1/2001 |
| EP | 0 601 417 | A2 | 6/1994 |
| EP | 0 662 611 | A2 | 7/1995 |
| EP | 2 698 636 | A1 | 2/2014 |
| EP | 2 727 597 | A1 | 5/2014 |
| JP | 2006-347993 | A | 12/2006 |
| RU | 2303461 | C9 | 12/2007 |
| WO | WO 1992/022301 | A1 | 12/1992 |
| WO | WO 1993/003375 | A1 | 2/1993 |
| WO | WO 1993/003735 | A1 | 3/1993 |
| WO | WO 1996/015810 | A1 | 5/1996 |
| WO | WO 1997/007810 | A1 | 3/1997 |
| WO | WO 1997/019105 | A1 | 5/1997 |
| WO | WO 1998/047915 | A1 | 10/1998 |
| WO | WO 1998/049558 | A1 | 11/1998 |
| WO | WO 1999/012944 | A2 | 3/1999 |
| WO | WO 1999/052561 | A1 | 10/1999 |
| WO | WO 1999/053757 | A1 | 10/1999 |
| WO | WO 2000/020871 | A1 | 4/2000 |
| WO | WO 2000/029439 | A1 | 5/2000 |
| WO | WO 2000/033887 | A2 | 6/2000 |
| WO | WO 2000/034296 | A2 | 6/2000 |
| WO | WO 2000/050447 | A1 | 8/2000 |
| WO | WO 2001/002018 | A2 | 1/2001 |
| WO | WO 2001/021660 | A1 | 3/2001 |
| WO | WO 2002/016414 | A2 | 2/2002 |
| WO | WO 2002/018950 | A1 | 3/2002 |
| WO | WO 2002/038592 | A2 | 5/2002 |
| WO | WO 2002/098459 | A2 | 12/2002 |
| WO | WO 2003/002127 | A1 | 1/2003 |
| WO | WO 2003/068822 | A2 | 8/2003 |
| WO | WO 2004/015420 | A1 | 2/2004 |
| WO | WO 2004/062599 | A2 | 7/2004 |
| WO | WO 2004/065400 | A1 | 8/2004 |
| WO | WO 2005/037293 | A1 | 4/2005 |
| WO | WO 2005/051429 | A2 | 6/2005 |
| WO | WO 2005/051920 | A2 | 6/2005 |
| WO | WO 2005/054264 | A2 | 6/2005 |
| WO | WO 2005/080985 | A2 | 9/2005 |
| WO | WO 2005/085264 | A1 | 9/2005 |
| WO | WO 2005/118609 | A2 | 12/2005 |
| WO | WO 2006/037979 | A2 | 4/2006 |
| WO | WO 2006/068720 | A2 | 6/2006 |
| WO | WO 2007/138263 | A1 | 12/2007 |
| WO | WO 2008/002449 | A2 | 1/2008 |
| WO | WO 2008/030505 | A2 | 3/2008 |
| WO | WO 2008/059003 | A1 | 5/2008 |
| WO | WO 2008/151847 | A1 | 12/2008 |
| WO | WO 2009/017795 | A1 | 2/2009 |
| WO | WO 2009/101475 | A2 | 8/2009 |
| WO | WO 2009/102820 | A2 | 8/2009 |
| WO | WO 2009/126933 | A2 | 10/2009 |
| WO | WO 2011/031472 | A2 | 3/2011 |
| WO | WO 2011/073685 | A1 | 6/2011 |
| WO | WO 2011/101870 | A1 | 8/2011 |
| WO | WO 2011/156774 | A2 | 12/2011 |
| WO | WO 2012/080444 | A1 | 6/2012 |
| WO | WO 2013/044044 | A2 | 3/2013 |
| WO | WO 2014/027302 | A1 | 2/2014 |
| WO | WO 2014/072330 | A1 | 5/2014 |
| WO | WO 2014/175838 | A1 | 10/2014 |
| WO | WO 2015/007326 | A1 | 1/2015 |
| WO | WO 2015/116775 | A1 | 8/2015 |
| WO | WO 2015/136027 | A1 | 9/2015 |
| WO | WO 2017/046172 | A1 | 3/2017 |

OTHER PUBLICATIONS

Burger, D. et al., "Anti-myelin-associated glycoprotein antibodies in patients with a monoclonal IgM gammopathy and polyneuropathy,and a simplified method for the preparation of glycolipid antigens," J Immunol Methods, vol. 140, Iss. 1, Jun. 24, 1991, pp. 31-36.

Byrne, G. W. et al., "Evaluation of different alpha-Galactosyl glycoconjugates for use in xenotransplantation," Bioconjugate Chem., vol. 13, Iss. 3, Mar. 26, 2002, pp. 571-581.

Crocker, P.R. et al., "Siglecs and their roles in the immune system," Nat Rev Immunol, vol. 7, Apr. 2007, pp. 255-266.

Dalakas, M. C., "Pathogenesis and treatment of anti-MAG neuropathy," Curr Treat Options Neurol, vol. 12, Iss. 2, Mar. 2010, pp. 71-83.

Davis, B. G. "Recent developments in glycoconjugates," J. Chem. Soc., vol. 1, Jun. 14, 1999, pp. 3215-3237.

Duthaler, R. O. et al., "In vivo neutralization of naturally existing antibodies against linear alpha(1,3)-galactosidic carbohydrate epitopes by multivalent antigen presentation: A solution for the first hurdle of pig-to-human xenotransplantation," Chimia, vol. 64, No. 1, Feb. 2010, pp. 23-28.

Fluri, F. et al., "Microheterogeneity of anti-myelinassociated glycoprotein antibodies," J Neurol Sci, vol. 207, Iss. 1-2, Mar. 2003, pp. 43-49.

Gallego et al., "Epitope Diversity of N-Glycans from Bovine Peripheral Myelin Glycoprotein PO Revealed by Mass Spectrometry and Nano Probe Magic Angle Spinning $^1$H NMR Spectroscopy," Journal of Biological Chemistry 276(33), Aug. 17, 2001, pp. 30334-30844.

Herrendorff et al., "Selective in vivo removal of pathogenic anti-MAG autoantibodies, an antigen-specific treatment option for anti-MAG neuropathy," Proceedings of the National Academy of Sciences USA 114(18), May 2, 2017, pp. E3689-E3698.

Herrendorff, R. et al., "Anti-myelin-associated glycoprotein neuropathy—a Carbohydrate Polymer Effectively Blocks Pathogenic Anti-MAG Antibodies," 13th International Congress on Neuromuscular Disease (ICNMD), Nice, France, Jul. 2014, Abstract, one page.

Holgersson, J. et al., "Characteristics of protein-carbohydrate interactions as a basis for developing novel carbohydrate-based antirejection therapies," Immunol Cell Biol, vol. 83, Oct. 21, 2005, pp. 694-708.

Ilyas, A. A. et al., "IgM in a human neuropathy related to paraproteinemia binds to a carbohydrate determinant in the myelin-associated glycoprotein and to a ganglioside," Proc Natl Acad Sci USA, vol. 81, Feb. 1984, pp. 1225-1229.

Ilyas, A. A. et al., "Induction of experimental ataxic sensory neuronopathy in cats by immunization with purified SGPG," J Neuroimmunol., vol. 193, No. 1-2, Jan. 2008, pp. 87-93.

Katopodis, A. G. et al., "Removal of anti-Galalpha1,3Gal xenoantibodies with an injectable polymer," J Clin Invest, vol. 110, No. 12, Dec. 2002, pp. 1869-1877.

Kelm, S. et al., "Sialoadhesin, myelin-associated glycoprotein and CD22 define a new family of sialic acid-dependent adhesion molecules of the immunoglobulin superfamily," Curr Biol, vol. 4, Iss. 11, Nov. 1994, pp. 965-972.

(56) References Cited

OTHER PUBLICATIONS

Kornilov, A. V. et al., "Synthesis of 3-O-sulfoglucuronyl lacto-N-neotetraose 2-aminoethyl glycoside and biotinylated neoglycoconjugates thereof," Carbohydr Res, vol. 329, Iss. 4, Dec. 2000, pp. 717-730.
Lunn, M. P. T. et al., "Immunotherapy for IgM anti-myelin-associated glycoprotein paraprotein-associated peripheral neuropathies," Cochrane Database Syst Rev, Oct. 2016, pp. 1-68.
Nifantiev, N. E. et al., "New schemes for the synthesis of glycolipid oligosaccharide chains," Pure Appl. Chem., vol. 76, Iss. 9, Sep. 30, 2004, pp. 1705-1714.
Oberg, C. T. et al., "Inhibition of Galectins with Small Molecules," Chimia, vol. 65, No. 1/2, Feb. 1, 2011, pp. 18-23.
Ogino, M. et al., "Affinity studies of human anti-MAG antibodies in neuropathy," J Neuroimmunol, vol. 52, Iss. 1, Jun. 1994, pp. 41-46.
Page, N. et al., "A monoclonal anti-idiotypic antibody against a human monoclonal IgM with specificity for myelin-associated glycoprotein," J Immunol, vol. 134, No. 5, May 1, 1985, pp. 3094-3099.
PCT International Search Report for PCT/EP2015/055140, dated May 4, 2015, four pages.
Quarles, R. H., "Myelin-associated glycoprotein (MAG): Past, present and beyond," J Neurochem, vol. 100, Nov. 9, 2006, pp. 1431-1448.
Russian Federal Service for Intellectual Property, Official Action (Inquiry) of the Substantive Examination, RU Patent Application No. 2016134035/04, dated Oct. 24, 2018, 14 pages.
Sarkar et al., "Synthesis and glycosaminoglycan priming activity of three disaccharides related to the linkage region tetrasaccharide of proteoglycans," Carbohydrate Research 279, Dec. 1995, pp. 161-171.
Sato, S. et al., "cDNA cloning and amino acid sequence for human myelin associated glycoprotein," Biochem Biophys Res Commun, vol. 163, Iss. 3, Sep. 29, 1989, pp. 1473-1480.
Schmitz, B. et al., "Determination of structural elements of the L2/HNK-1 carbohydrate epitope required for its function", Glycoconjugate Journal, vol. 11, Iss. 4, Aug. 1994, pp. 345-352.
Simon-Haldi et al., "Identification of a peptide mimic of the L2/HNK-1 carbohydrate epitope," Journal of Neurochemistry 83(6), Dec. 2002, pp. 1380-1388.
Spagnol, G. et al., "Molecular cloning of human myelin-associated glycoprotein,". J Neurosci Res, vol. 24, Oct. 1989, pp. 137-142.
Sukhova, E. V. et al., "Synthesis of oligosaccharides related to the HNK-1 antigen. 5. Synthesis of a sulfo-mimetic of the HNK-1 antigenic trisaccharide", Russian Chemical Bulletin, International Edition, vol. 56, No. 8, Aug. 2007, pp. 1655-1670.
Tatum, A. H., "Experimental paraprotein neuropathy, demyelination by passive transfer of human IgM anti-myelin-associated glycoprotein," Ann Neurol, vol. 33, May 1993, pp. 502-506.
Tokuda, A. et al., "On the specificity of anti-sulfoglucuronosyl glycolipid antibodies," J Carbohydr Chem, vol. 17, 1998, pp. 535-546.
Tsvetkov et al., "Synthesis and Molecular Recognition Studies of the HNK-1 Trisaccharide and Related Oligosaccharides. The Specificity of Monoclonal Anti-HNK-1 Antibodies as Assessed by Surface Plasmon Resonance and STD NMR," Journal of the American Chemical Society 134(1), Jan. 11, 2012, pp. 426-435.
Usuki, S. et al., "Development of a novel therapy for Lipo-oligosaccharide-induced experimental neuritis Use of peptide glycomimics," J Neurochem, vol. 113, Apr. 2010, pp. 351-362.
Usuki, S. et al., "Novel anti-idiotype antibody therapy for lipooligosaccharide-induced experimental autoimmune neuritis: Use relevant to Guillain-Barré syndrome," J Neurosci Res, vol. 88, Iss. 8, Jun. 2010, pp. 1651-1663.
Voshol et al., "Structure of the HNK-1 Carbohydrate Epitope on Bovine Peripheral Myelin Glycoprotein PO," Journal of Biological Chemistry 271 (38), Sep. 13, 1996, pp. 22957-22960.
Willison, H. J. et al., "Synthetic disialylgalactose immunoadsorbents deplete anti-GQ1b antibodies from autoimmune neuropathy sera," Brain, vol. 127, Iss. 3, Mar. 2004, pp. 680-691.
Zsiska et al., "Influence of sulfate and carboxylate groups on the conformation of chondroitin sulfate related disaccharides," Carbohydrate Research, vol. 243, Iss. 2, May 7, 1993, pp. 225-258.
Zsiska et al., "Synthesis of beta-D-GlcA-(173)-beta-D-Gal disaccharides with 4- and 6- sulfate groups and 4,6-disulfate groups," Carbohydrate Research 215(2), Aug. 20, 1991, pp. 279-292.
Miyase, T. et al., "Linderniosides A and B, Oleanane Saponins From Lindernia Pyxidaria," Phytochemistry, vol. 40, No. 5, Nov. 1995, pp. 1499-1502.
Munneke, S. et al., "The Rapid and Facile Synthesis of Oxyamine Linkers for the Preparation of Hydrolytically Stable Glycoconjugates," Organic Letters, vol. 17, No. 3, Jan. 16, 2015, pp. 624-627.
Skaar, I. et al., "Purple anthocyanin colouration on lower (abaxial) leaf surface of Hemigraphis colorata (Acanthaceae)," Phytochemistry, vol. 105, Jun. 20, 2014, pp. 141-146.
Thoma, G. et al., "Nanomolar E-Selectin Inhibitors: 700-Fold Potentiation of Affinity by Multivalent Ligand Presentation," Journal of the American Chemical Society, vol. 123, No. 41, Sep. 22, 2001, pp. 10113-10114.
Willison, H.J. et al., "Peripheral neuropathies and anti-glycolipid antibodies," Brain, col. 125, Iss. 12, Dec. 2002, pp. 2591-2625.
Al-Jamal, K. T. et al., "An intrinsically fluorescent dendrimer as a nanoprobe of cell transport," Journal of Drua Taraetina, vol. 14, No. 6, Jul. 2006, pp. 405-412.
Ariga, T., "Pathogenic role of ganglioside metabolism in neurodegenerative diseases," Journal of Neuroscience Research, vol. 92, Iss. 10, Oct. 2014, pp. 1227-1242.
Berentsen, S., "Role of Complement in Autoimmune Hemolytic Anemia," Transfus Med Hemother, vol. 42, No. 5, Sep. 2015, pp. 303-310.
Bohorov, O. et al., "Arraying glycomics: a novel bi-functional spacer for one-step microscale derivatization of free reducing glycans," Glycobiology 16(12), Dec. 2006, pp. 21C-27C.
Braun, P.E. et al., "Myelin-associated glycoprotein is the antigen for a monoclonal IgM in polyneuropathy," Journal of Neurochemistry, vol. 39, Iss. 5, Nov. 1982, pp. 1261-1265.
Bukowski, R. et al., "Synthesis and Conformational Analysis of the T-Antigen Disaccharide (13-D-Gal-(1->3)-a-D-GalNAc-OMe)," European Journal of Organic Chemistry, vol. 2001, Iss. 14, Jul. 2001, pp. 2697-2705.
Crew, V. K. et al., "New mutations in C1 GAL T1 C1 in individuals with Tn positive phenotype," British Journal of Haematology, vol. 142, No. 4, Jun. 5, 2008, DD. 657-667.
Das, S. et al., "Neutralization of cholera toxin with nanoparticle decoys for treatment of cholera," PLOS Neglected Tropical Diseases 12(2), Feb. 22, 2018, pp. 1-17.
Delmont, E. et al., "Diagnostic Utility of Auto Antibodies in Inflammatory Nerve Disorders," Journal of Neuromuscular Diseases, vol. 2, Jun. 4, 2015, pp. 107-112.
Ernst, B. et al., "From carbohydrate leads to glycomimetic drugs," Nature Reviews Drug Discovery, Jul. 24, 2009, pp. 661-677.
Esko, J. D. et al., "Microbial Lectins: Hemagglutinins, Adhesins, and Toxins," Essentials of Glycobiology, Chapter 34, 2nd edition, 2009, seven pages, [Online] [Retrieved on Jan. 10, 2020] Retrieved from the Internet <URL: https://www.ncbi.nlm. nih.aov/books/ NBK1907 /?report=reader>.
Furuike, T., et al., "A Highly Practical Synthesis of Cyclodextrin-Based Glycoclusters Having Enhanced Affinity with Lectins," Tetrahedron, 2000, vol. 56, No. 51, pp. 9909-9915.
Furukawa, T. et al., "A potential glucuronate glycosyl donor with 2-O-acyl-6,3-lactone structure: efficient synthesis of glycosaminoglycan disaccharides," Tetrahedron Letters, vol. 52, Iss. 43, Oct. 26, 2011, pp. 5567-5570.
Gabriel, J-M. et al., "Confocal microscopic localization of anti-myelin-associated glycoprotein autoantibodies in a patient with peripheral neuropathy initially lacking a detectable IgM gammopathy," Acta Neuropathologica, vol. 95, Apr. 1998, pp. 540-546.
Halkes, K.M. et al., "A Facile Method for the Preparation of Gold Glyconanoparticles from Free Oligosaccharides and Their Applicability in Carbohydrate-Protein Interaction Studies," Eur. J. Org. Chem, vol. 2005, No. 17, Aug. 15, 2005, pp. 3650-3659.

(56) References Cited

OTHER PUBLICATIONS

Kadlecova, Z. et al., "Comparative Study on the In Vitro Cytotoxicity of Linear, Dendritic, and Hyperbranched Polylysine Analogues," Biomacromolecules, vol. 13, No. 10, Aug. 29, 2012, pp. 3127-3137.
Karki, G. et al., "An expeditious synthesis of blood-group antigens, ABO histo-blood group type II antigens and xenoantigen oligosaccharides with amino type spacer-arms," Glycoconjugate Journal, vol. 33, Feb. 2016, pp. 63-78.
Knoppova, B. et al., "The Origin and Activities of igA1-Containing immune Complexes in igA Nephropathy," Frontiers in Immunology, vol. 7, Article 117, Apr. 2016, pp. 1-25.
Kollewe, K. et al., "Anti-Ganglioside Antibodies in Amyotrophic Lateral Sclerosis Revisited," Plos One, Apr. 14, 2015, pp. 1-11.
Millen, S. H. et al., "Identification and Characterization of the Carbohydrate Ligands Recognized by Pertussis Toxin via a Glycan Microarray and Surface Plasmon Resonance," Biochemistry, vol. 49, No. 28, Jun. 1, 2010, pp. 5954-5967.
Nagatsuka, T. et al., "Glycotechnology for Decontamination of Biological Agents: A Model Study Using Ricin and Biotin-Tagged Synthetic Glycopolymers," ACS Applied Materials & Interfaces, vol. 4, No. 2, Jan. 2, 2012, pp. 832-837.
Nobile-Orazio, E et al., "Treatment of patients with neuropathy and anti-MAG IgM M-proteins," Annals of Neurology, vol. 24, Iss. 1, Jul. 1988, pp. 93-97.
Numa Ta, M et al., "Total synthesis of sialosylcerebroside, GM4," Carbohydrate Research, vol. 163, Iss. 2, Jun. 1987, pp. 209-225.
PCT International Search Report & Written Opinion, International Application No. PCT/EP2018/056583, dated Jun. 12, 2018, 14 Pages.
PCT International Search Report for PCT/EP2016/071711, dated Oct. 26, 2016.
PCT Third Party Observations, International Application No. PCT/EP2018/056583, dated Jul. 12, 2019, 15 pages.
Polizzotti, B.D. et al., "Effects of Polymer Structure on the Inhibition of Cholera Toxin by Linear Polypeptide-Based Glycopolymers," Biomacromolecules 7(2), Feb. 2006, pp. 483-490.
Pukin, AV., et al., "Strong Inhibition of Cholera Toxin by Multivalent GM1 Derivatives," ChemBioChem, 2007, vol. 8, No. 13, Paaes 1500-1503.
Richards, S. J, et al., "Probing bacterial-toxin inhibition with synthetic glycopolymers prepared by tandem post-polymerization modification: role of linker length and carbohydrate density," Angewandte, Chemie International Edition, vol. 51, Iss. 31, Jun. 19, 2012, pp. 7812-7816.
Schneller, M., et al., "An Effective Method for the Synthesis of Neoglycoproteins and Neogangliosideproteins by Use of Reductively Aminated Sulfhydryl-Containing Carbohydrate Conjugates," Biol. Chem. Hoppe-Seyler, 1992, vol. 373, No. 11, pp. 1095-1104.
Sheikh, K.A. et al., "An update on pathobiologic roles of anti-glycan antibodies in Guillain-Barre syndrome," Biology Reports, vol. 2, No. 21, Mar. 25, 2010, pp. 1-5.
Song, E.H. et al., "In vivo targeting of alveolar macrophages via RAFT-based glycopolymers," Biomaterials 33(28), Jul. 5, 2012, pp. 6889-6897.
Steck, A.J. et al., "Anti-myelin-associated glycoprotein neuropathy," Current Opinion in Neurology, vol. 19, Iss. 5, Oct. 2006, pp. 458-463.
Steck, A.J. et al., "Demyeliating neuropathy and monoclonal IgM antibody to myelin-associated glycoprotein," Neurology, vol. 33, Iss. 1, Jan. 1, 1983, pp. 19-23.
Stevenson, L. et al., "Investigating the function of Fc-specific binding of IgM to Plasmodium falciparum erythrocyte membrane protein 1 mediating erythrocyte resetting," Cellular Microbiology, vol. 17, Iss. 6, Jan. 28, 2015, pp. 819-831.
Sun, B. et al., "Total synthesis of the aminopropyl functionalized ganglioside GM1 ," Science China Chemistry, vol. 55, Iss. 1, Jan. 2012, pp. 31-35.
Thoma, G. et al., "Synthesis of Oligosaccharide-Polylysine Conjugates: A Well Characterized Sialyl Lewisa Polymer for ELISA," J. Am. Chem. Soc., vol. 119, No. 31, Aug. 6, 1997, pp. 7414-7415.
Thoma, G. et al., "Versatile Functionalization of Polylysine: Synthesis, Characterization, and Use of Neoglycoconjugates," J. Am. Chem. Soc., vol. 121, No. 25, Jun. 11, 1999, pp. 5919-5929.
Ueda, A. et al., "Anti-GM1 antibodies affect the integrity of lipid rafts," Molecular and Cellular Neuroscience, vol. 45, Iss. 4, Dec. 2010, pp. 355-362.
Ueda, I. et al., "Synthesis and Pharmacological Properties of N-[3-{3-(1-Piperidinylmethyl)phenoxy}propyl]-2-(2-hydroxyethylthio)acetamide and Related Compounds as Antiulcer Agents.I," Chemical and Pharmaceutical Bulletin, vol. 38, No. 11, Nov. 1990, pp. 3035-3041.
United States Office Action, U.S. Appl. No. 15/760,398, dated Sep. 29, 2020, 17 pages.
Watanabe, M. et al., "Structural Analysis of the Interaction between Shiga Toxin B Subunits and Linear Polymers Bearing Clustered Globotriose Residues," Infection and Immunity, vol. 74, No. 3, Mar. 2006, pp. 1984-1988.
Willison, H.J. et al., "Glycolipid antigens and autoantibodies in autoimmune neuropathies," Trends in Immunology, vol. 34, Iss. 9, Sep. 2013, pp. 453-459.
Wilson, J. W et al., "Mechanisms of bacterial pathogenicity," Postgraduate Medical Journal, vol. 78, Apr. 1, 2002, pp. 216-224.
Yeh, C-Y. et al., "C-Terminal Repeats of Clostridium difficile Toxin A Induce Production of Chemokine and Adhesion Molecules in Endothelial Cells and Promote Migration of Leukocytes," Infection and Immunity, vol. 76, No. 3, Mar. 2008, pp. 1170-1178.
Zhang, Z. et al., "Programmable One-Pot Oligosaccharide Synthesis," Journal of the American Chemical Society, vol. 121, No. 4, Jan. 14, 1999, pp. 734-753.
Zhou, D. et al., "Glycopolymer modification on physicochemical and biological properties of poly(L-lysine) for gene delivery," International Journal of Biological Macromolecules, vol. 50, Iss. 4, May 2012, pp. 965-973.

2(a)

2(b)

2(c)

2(d)

2(e)

CARBOHYDRATE LIGANDS THAT BIND TO IGM ANTIBODIES AGAINST MYELIN-ASSOCIATED GLYCOPROTEIN

FIELD OF THE INVENTION

The invention relates to carbohydrate ligands that bind to IgM antibodies against myelin-associated glycoprotein (MAG), polymers comprising these, and to their use in diagnosis and therapy of anti-MAG neuropathy.

BACKGROUND OF THE INVENTION

Anti-myelin-associated glycoprotein neuropathy is a demyelinating peripheral neuropathy, caused by autoantibodies recognizing the antigenic HNK-1 carbohydrate epitope, found on myelin-associated glycoprotein (MAG) and other glycoconjugates of the peripheral nervous system (PNS). The clinical picture is characterized by a slowly progressing demyelinating, predominantly sensory neuropathy. The correlation of high levels of antibodies and demyelination is well established. Thus, pathological studies on nerve biopsies from patients show demyelination and widening of myelin lamellae, as well as deposits of anti-MAG IgM on myelin. Furthermore, therapeutic reduction of the IgM antibody concentration leads to clinical improvement of neuropathic symptoms. (A. J. Steck et al., Current Opinion in Neurology 2006, 19:458-463; M. C. Dalakas, Current Treatment Options in Neurology 2010, 12:71-83).

The myelin glycoconjugates that contain the HNK-1 epitope include the glycoproteins MAG, protein zero (P0), peripheral myelin protein-22 (PMP22), as well as the glycolipids sulfoglucuronyl paragloboside (SGPG) and sulfoglucuronyl lactosaminyl paragloboside (SGLPG). Several observations suggest MAG as major target for the IgM antibodies: (i) Deposits of patients' antibodies to PNS sites are co-localized with MAG, (ii) MAG is selectively lost from myelin, and (iii) the human nerve pathology and MAG-knockout mice show characteristic similarities (R. H. Quarles, Journal of Neurochemistry 2007, 100: 1431-1448).

MAG belongs to the family of sialic acid-binding immunoglobulin-like lectins (Siglecs). It is located mainly in periaxonal membranes of oligodendroglial cells in the CNS and Schwann cells in the PNS and is involved in adhesion and signaling processes at the axon-glia interface (R. H. Quarles, 2007, loc. cit.). MAG is strongly glycosylated, i.e. 30% of its molecular weight is contributed by heterogeneous N-linked oligosaccharides. All of the potential eight N-glycosylation sites of MAG can carry the HNK-1 epitope. The two glycolipids (SGPG, SGLPG) carrying the HNK-1 epitope contain 3-O-sulfoglucuronic acid ($SO_3$-3GlcA) as a specific hallmark (T. Ariga et al., J Biol Chem 1987, 262:848-853). Interestingly, the HNK-1 epitope structure of bovine glycoprotein PO also contains this characteristic feature. The similarity between the three elucidated structures is restricted to the terminal trisaccharide. Consequently the HNK-1 epitope was defined as $SO_3$-3-GlcA(β1-3)Gal(β1-4)GlcNAc—OH.

The precise carbohydrate epitope recognized by IgM antibodies remains unclear. A study with SGPG derivatives showed that the IgM antibodies place different importance on the carboxyl and the sulfate group. Whereas "intact" SGPG, containing both negatively charged groups, was reported as optimal epitope for antibody binding (A. A. Ilyas et al., J Neurochemistry 1990, 55:594-601), other studies emphasize the importance of the length of the carbohydrate chain for antibody recognition. Furthermore, the $SO_3$-3-GlcA(β1-3)Gal disaccharide epitope seems to be the minimum requirement for binding (A. Tokuda et al., J. Carbohydrate Chemistry 1998, 17:535-546).

SUMMARY OF THE INVENTION

The invention relates to carbohydrate ligands that bind to anti-MAG IgM antibodies, and their use in diagnosis as well as for the treatment of anti-MAG neuropathy.

In particular the invention relates to disaccharides of formula (I)

(I)

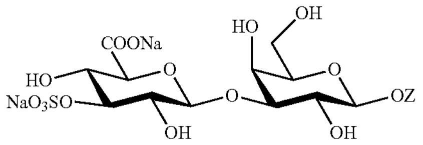

and of formula (II)

(II)

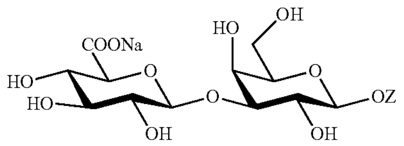

wherein Z is optionally substituted phenyl, heteroaryl, arylcarbonyl, or heteroarylmethyl.

Furthermore the invention relates to therapeutically acceptable polymers comprising a multitude of substituents of formula (I) and/or formula (II), wherein Z is a linker connecting said substituent to the polymer backbone.

The invention relates also to pharmaceutical compositions comprising these compounds, diagnostic kits containing these, and to the use of these compounds for the diagnosis and therapy of anti-MAG neuropathy.

Figure 1:
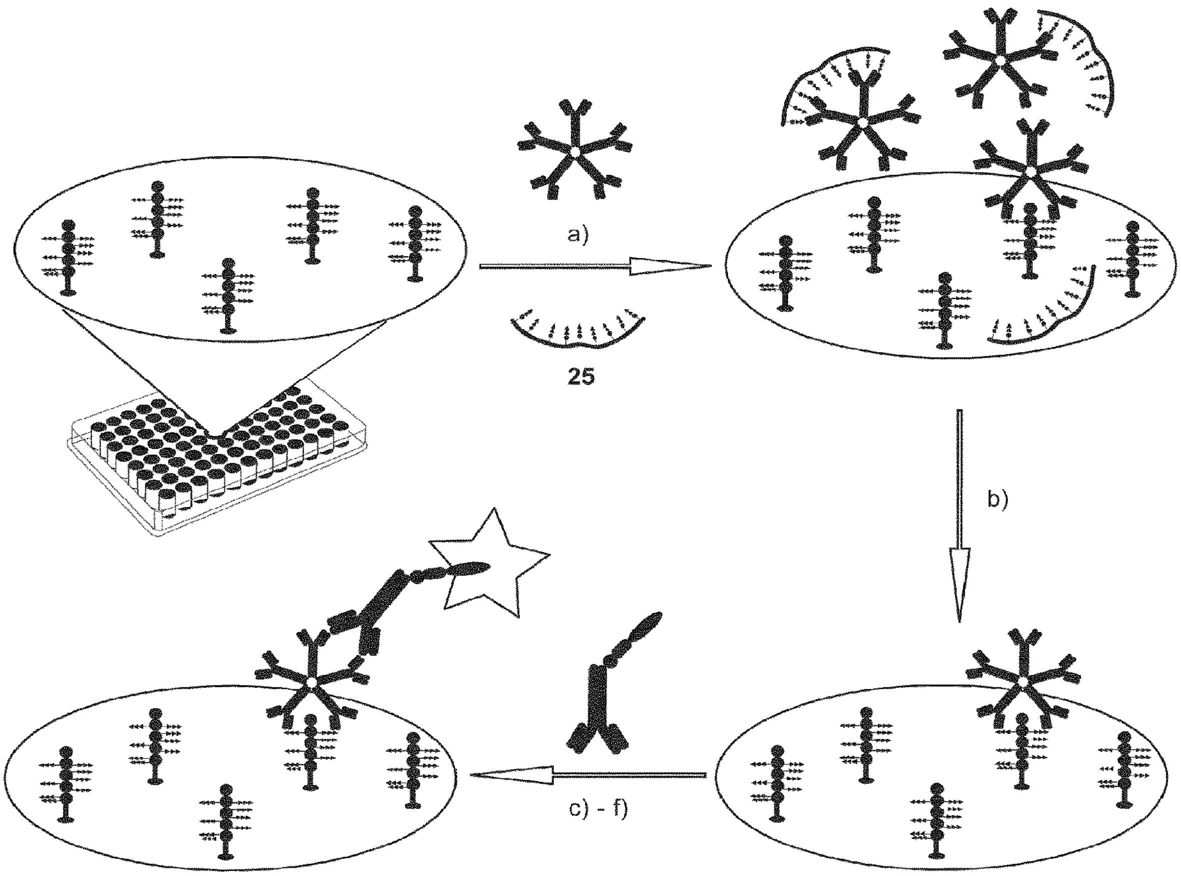
FIG. 1. Schematic representation of a competitive binding assay (a) Incubation of MAG-coated plates with anti-MAG IgM (patient sera) and polymer 25. (b) Wash step. (c) Incubation with anti-human IgM antibody coupled to horseradish peroxidase. (d) Wash step. (e) Addition of tetramethylbenzidin (TMB) substrate. (f) Addition of acidic stop solution and measurement of the optical density.

2(*a*) The MAG-coated wells were co-incubated with compound 1 (50 mM highest concentration) and the four patient sera MK, DP, KH and SJ (% ab=% IgM antibody binding to MAG).

2(*b*) Co-incubation of MAG-coated wells with compound 2 (50 mM highest concentration) together with patient sera MK and SJ.

2(*c*) Co-incubation with compound 25 (15 μM highest concentration) together with patient sera MK, KH and SJ. Compound 25 is a polylysine polymer with a defined percentage of lysine residues coupled to the minimal HNK-1 epitope (1). The general abbreviation used is as follows: PL(minHNK-1)$_x$ with x defining the percentage of epitope loading in %. In this case the polymer is PL(minHNK-1)$_{44}$.

2(*d*) Co-incubation with patient serum KH together with the polymers PL(minHNK-1)$_x$ with x being 10, 25, 31 and 44% (0.5 mM highest concentration).

2(*e*) Co-incubation with the mouse monoclonal anti-HNK-1 IgM antibody, a positive control antibody, together with the polymers PL(minHNK-1)$_x$ with x being 10, 25, 31 and 44% (0.5 mM highest concentration).

DETAILED DESCRIPTION OF THE INVENTION

A minimal HNK-1 carbohydrate epitope still reliably recognized by anti-MAG IgM antibodies was identified and corresponding disaccharides prepared both in a sulfated (formula I) and non-sulfated form (formula II).

The invention relates to these disaccharides of formula (I)

(I)

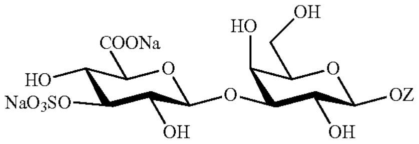

and of formula (II)

(II)

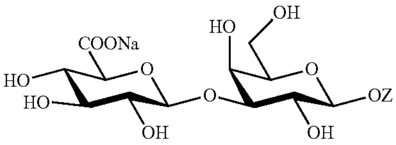

wherein Z is optionally substituted phenyl, heteroaryl, arylcarbonyl, or heteroarylmethyl. The sulfate moiety in formula (I) is located in position 3 of glucuronic acid.

Furthermore the invention relates to polymers comprising a multitude of substituents of formula (I) and/or formula (II), wherein Z is a linker connecting said substituent to the polymer backbone.

In particular, linker Z is (bifunctional) aryl, heteroaryl, aryl-lower alkyl, arylcarbonyl, or heteroarylmethyl, wherein aryl or heteroaryl is substituted by alkylene with 3 to 25 carbon atoms connecting to the polymer wherein optionally (a) one or more carbon atoms of alkylene are replaced by nitrogen carrying a hydrogen atom, and one of the adjacent carbon atoms is substituted by oxo, representing an amide function —NH—CO—; and/or (b) one or more carbon atoms of alkylene are replaced by oxygen;

(c) one or more carbon atoms of alkylene are replaced by sulphur; and/or (d1) the terminal carbon atom connecting to the polymer is substituted by oxo; or (d2) the terminal carbon atom connecting to the polymer is replaced by —NH—.

The polymer comprising the multitude of substituents of formula (I) and/or formula (II), wherein Z is a linker connecting said substituent to the polymer backbone, is preferably an α-amino acid polymer, an acrylic acid or methacrylic acid polymer or copolymer, or a N-vinyl-2-pyrrolidone-vinylalcohol copolymer.

Particular examples of polymers of the invention are (A) a poly-α-amino acid, wherein the amino acid carries a side chain aminoalkyl function, such as in poly-lysine, in particular poly-L-lysine or poly-D-lysine, and the amino group is connected to a terminal carbonyl group of bifunctional linker Z;

(B) a poly-α-amino acid, wherein the amino acid carries a side chain carbonylalkyl function, such as in poly-aspartic acid or poly-glutamic acid, and the carbonyl group (which corresponds to the original carboxy group in aspartic acid and glutamic acid, respectively) is connected to a terminal —$CH_2$-group of bifunctional linker Z;

(C) poly-acrylic acid, poly-methacrylic acid or a copolymer of acrylic and methacrylic acid, wherein the carboxy group is amidated by a terminal amino group of bifunctional linker Z; and (D) a copolymer of N-vinyl-2-pyrrolidone and vinyl alcohol, wherein the hydroxy group of the vinyl alcohol part of the copolymer is connected to a terminal carbonyl group of bifunctional linker Z.

In a particular embodiment, a polymer (A) comprises the partial formula (III)

(III)

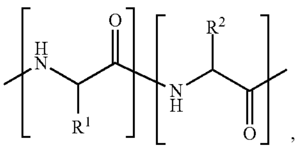, wherein $R^1$ is an aminoalkyl substituent connected to linker Z, wherein the alkylene group of Z carries an oxo group in the terminal position connected to the amino group of $R^1$, $R^2$ is 2,3-dihydroxypropylthioacetyl-aminoalkyl, and the relation between the two bracketed entities with $R^1$ and $R^2$, respectively, in the polymer indicates the relation of disaccharide loading to capped amino function.

For example, $R^1$ is of formula (IIIa)

(IIIa)

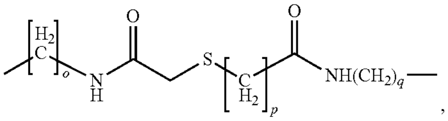, and $R^2$ is of formula (IIIb)

(IIIb)

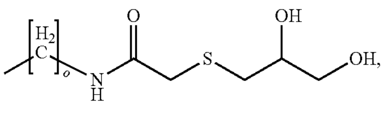

wherein o is between 1 and 6, preferably 3 or 4, p is between 1 and 6, preferably between 2 and 4, in particular 3, and q is between 1 and 6, preferably between 1 and 4, in particular 2.

When o is 3, substituent $R^1$ represents a side chain of poly-ornithine, and when o is 4, substituent $R^1$ represents a side chain of poly-lysine, connected to a linker Z carrying a disaccharide of formula (I) or (II) at the free valence, and $R^2$ is 2,3-dihydroxy-propylthioacetyl-aminoalkyl, i.e. a capped amino function having a solubilizing substituent.

The poly-amino acid can be linear, hyperbranched or dendritic, as described by Z. Kadlecova et al., Biomacromolecules 2012, 13:3127-3137, for poly-lysine as follows:
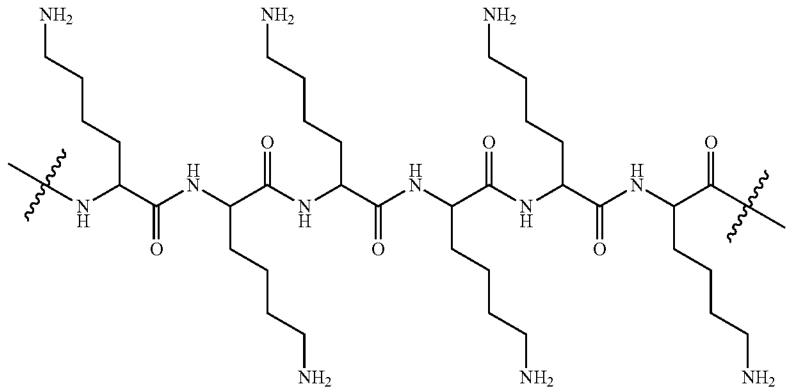
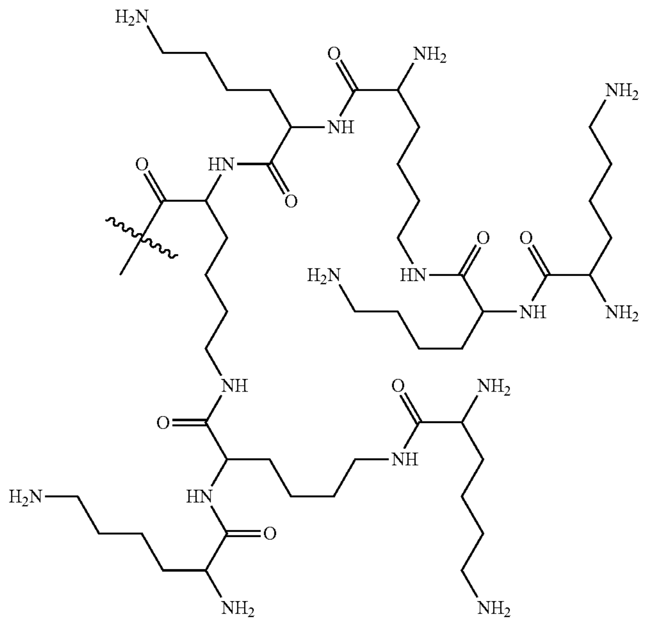

-continued

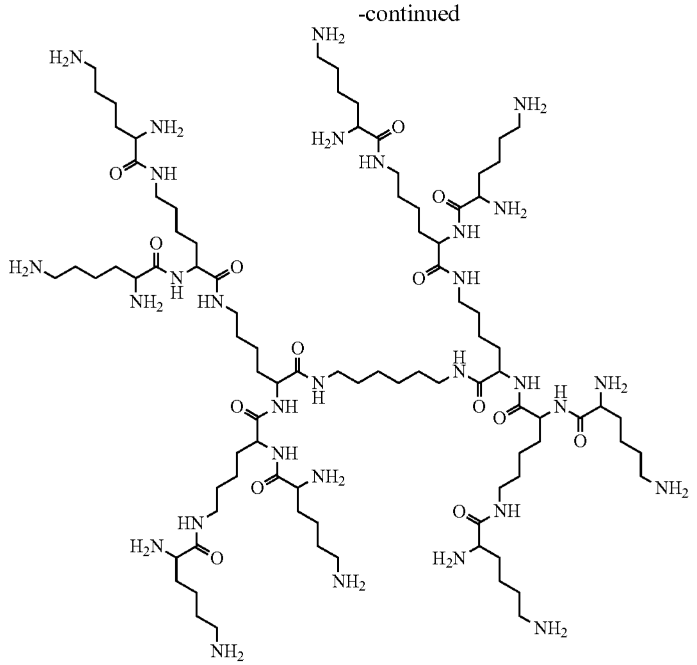

The poly-lysine used to prepare polymer (A) of formula (III) has preferably a molecular weight between 15,000 and 300,000, in particular 30,000 to 70,000, and such polymers further connected via a linker Z to compounds of formula (I) and/or (II) and with a capping 2,3-dihydroxypropylthio-acetyl residue are preferred.

In a particular embodiment, a polymer (B) comprises the partial formula (III)

(III)

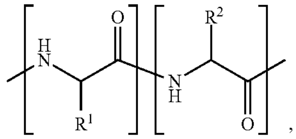

wherein $R^1$ is a carbonylalkyl substituent connected to linker Z, wherein the alkylene group of Z carries a —$CH_2$-group in the terminal position connected to the carbonyl group of $R^1$, $R^2$ is 2,3-dihydroxypropylthioacetyl-carbonylalkyl, and the relation between the two bracketed entities with $R^1$ and $R^2$, respectively, in the polymer indicates the relation of disaccharide loading to capped carbonyl or carboxy function.

For example, $R^1$ is of formula (IIIc)

(IIIc)

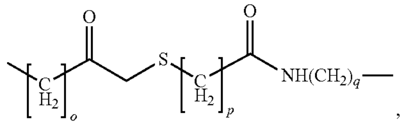

and $R^2$ is of formula (IIId)

(IIId)

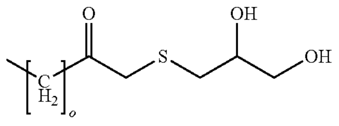

wherein o is between 1 and 6, preferably 1 or 2, p is between 1 and 6, preferably between 2 and 4, in particular 3, and q is between 1 and 6, preferably between 1 and 4, in particular 2.

When o is 1, substituent $R^1$ represents a side chain of poly-glutamic acid, and when o is 2, substituent $R^1$ represents a side chain of poly-aspartic acid, connected to a linker Z carrying a disaccharide of formula (I) or (II) at the free valence, and $R^2$ is 2,3-dihydroxy-propylthioacetyl-carbonyl-alkyl, i.e. a capped carboxy function having a solubilizing substituent.

The poly-aspartic acid used to prepare polymer (B) of formula (III) has preferably a molecular weight between 15,000 and 300,000, in particular 30,000 to 70,000, and such polymers further reacted with linker Z connected to compounds of formula (I) and/or (II) and with a capping 2,3-dihydroxypropylthioalkyl residue are preferred.

In a particular embodiment, a polymer (C) comprises the partial formula (IV)

(IV)

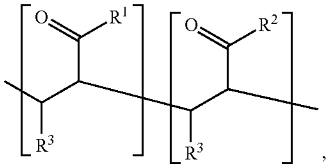

wherein $R^1$ is a linker Z, wherein the alkylene group of Z carries a —$NH_2$— group in the terminal position connected to the carbonyl group in (IV), $R^2$ is 2,3-dihydroxypropylthioacetylaminoalkylamino or a related amino substituent, and $R^3$ is hydrogen or methyl;

and the relation between the two bracketed entities with $R^1$ and $R^2$, respectively, in the polymer indicates the relation of disaccharide loading to capped carboxy function.

For example, $R^1$ is of formula (IVa)

(IVa)

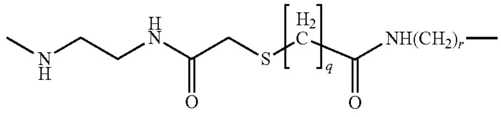

, and $R^2$ is of formula (IVb)

(IVb)

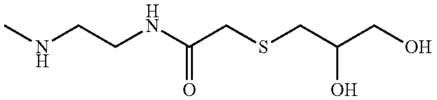

or (IVc)

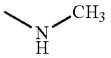

wherein in q is between 1 and 6, preferably between 4 and 6, and r is between 1 and 6, preferably between 1 and 4, in particular 2.

In another embodiment $R^1$ is of formula (IVd)

(IVd)

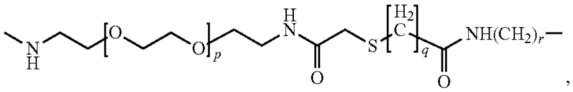

, and $R^2$ is of formula (IVe)

(IVe)

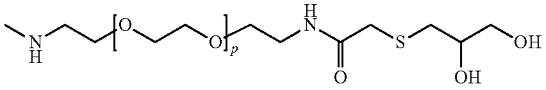

wherein p is between 1 and 10, preferably between 1 and 4, q is between 1 and 6, preferably between 4 and 6, and r is between 1 and 6, preferably between 1 and 4, in particular 2.

In another embodiment $R^1$ is of formula (IVf)

(IVf)

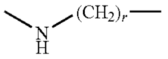

wherein r is between 1 and 6, preferably between 1 and 4, in particular 2, and $R^2$ is of formula (IVc) (above).

The poly-acrylic acid used to prepare polymer (C) of formula (IV) has preferably a molecular weight between 30,000 and 400,000, in particular 30,000 to 160,000, and such polymers further reacted with linker Z connected to compounds of formula (I) and/or (II) and with a capping 2,3-dihydroxypropylthioacetyl residue are preferred.

In a particular embodiment, a polymer (D) comprises the partial formula (V)

(V)

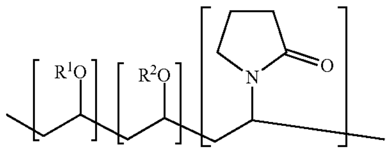

wherein $R^1$ is a linker Z, wherein the alkylene group of Z carries a aminocarbonyl group in the terminal position connected to the hydroxyl group in (V), $R^2$ is 2,3-dihydroxypropylthioacetylaminoalkylaminocarbonyl or a related aminocarbonyl substituent, and the relation between the two bracketed entities with $R^1$ and $R^2$, respectively, in the polymer indicates the relation of disaccharide loading to capped hydroxy function.

For example, $R^1$ is of formula (Va)

(Va)

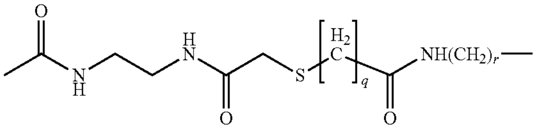

, and $R^2$ is of formula (Vb)

(Vb)

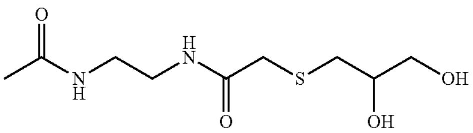

wherein q is between 1 and 6, preferably between 4 and 6, and r is between 1 and 6, preferably between 1 and 4, in particular 2.

In another embodiment $R^1$ is of formula (Vc)

(Vc)

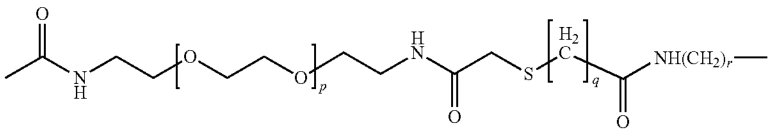

, and $R^2$ is of formula (Vd)

(Vd)

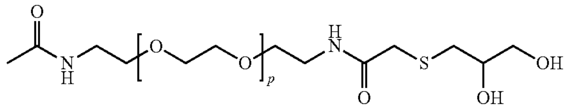

wherein p is between 1 and 10, preferably between 1 and 4, q is between 1 and 6, preferably between 4 and 6, and r is between 1 and 6, preferably between 1 and 4, in particular 2.

In another embodiment $R^1$ is of formula (Ve)

(Ve)

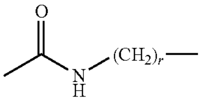

and $R^2$ is of formula (Vf)

(Vf)

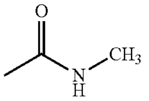

wherein r is between 1 and 6, preferably between 1 and 4, in particular 2.

The copolymer used to prepare polymer (D) of formula (V) has preferably a molecular weight between 30,000 and 400,000, in particular 30,000 to 160,000, and such polymers further reacted with linker Z connected to compounds of formula (I) and/or (II) and with a capping 2,3-dihydroxypropylthioacetyl residue are preferred.

The general terms used hereinbefore and hereinafter preferably have within the context of this disclosure the following meanings, unless otherwise indicated:

The prefix "lower" denotes a radical having up to and including a maximum of 7, especially up to and including a maximum of 4 carbon atoms, the radicals in question being either linear or branched with single or multiple branching.

Where the plural form is used for compounds, salts, and the like, this is taken to mean also a single compound, salt, or the like.

Double bonds in principle can have E- or Z-configuration. The compounds of this invention may therefore exist as isomeric mixtures or single isomers. If not specified both isomeric forms are intended.

Any asymmetric carbon atoms may be present in the (R)-, (S)- or (R,S)-configuration, preferably in the (R)- or (S)-configuration. The compounds may thus be present as mixtures of isomers or as pure isomers, preferably as enantiomer-pure diastereomers.

Alkyl (or bifunctional alkylene in a linker) has from 1 to 25, for example 1 to 12, preferably from 1 to 7 carbon atoms, and is linear or branched. Alkyl is preferably lower alkyl.

Preferably, (bifunctional) alkylene has from 3 to 25, preferably from 4 to 12 carbon atoms.

Lower alkyl has 1 to 7, preferably 1 to 4 carbon atoms and is butyl, such as n-butyl, sec-butyl, isobutyl, tert-butyl, propyl, such as n-propyl or isopropyl, ethyl or methyl. Preferably lower alkyl is methyl or ethyl.

Cycloalkyl has preferably 3 to 7 ring carbon atoms, and may be unsubstituted or substituted, e.g. by lower alkyl or lower alkoxy. Cycloalkyl is, for example, cyclohexyl, cyclopentyl, methylcyclopentyl, or cyclopropyl, in particular cyclopropyl.

Aryl stands for a mono- or bicyclic fused ring aromatic group with 5 to 10 carbon atoms optionally carrying substituents, such as phenyl, 1-naphthyl or 2-naphthyl, or also a partially saturated bicyclic fused ring comprising a phenyl group, such as indanyl, indolinyl, dihydro- or tetrahydronaphthyl, all optionally substituted. Preferably, aryl is phenyl, indanyl, indolinyl or tetrahydronaphthyl, in particular phenyl.

The term "aryl carrying substituents" stands for aryl substituted by up to four substituents independently selected from lower alkyl, halo-lower alkyl, cycloalkyl-lower alkyl, carboxy-lower alkyl, lower alkoxycarbonyl-lower alkyl; arylalkyl or heteroarylalkyl, wherein aryl or heteroaryl are unsubstituted or substituted by up to three substituents selected from lower alkyl, cyclopropyl, halo-lower alkyl, lower alkoxy, hydroxysulfonyl, aminosulfonyl, tetrazolyl, carboxy, halogen, amino, cyano and nitro; hydroxy-lower alkyl, lower alkoxy-lower alkyl, aryloxy-lower alkyl, heteroaryloxy-lower alkyl, aryl-lower alkoxy-lower alkyl, heteroaryl-lower alkoxy-lower alkyl, lower alkoxy-lower alkoxy-lower alkyl; aminoalkyl wherein amino is unsubstituted or substituted by one or two substituents selected from lower alkyl, hydroxy-lower alkyl, alkoxy-lower alkyl and amino-lower alkyl, or by one substituent alkylcarbonyl or mercaptoalkylcarbonyl, alkoxycarbonyl, amino-lower alkoxycarbonyl, lower alkoxy-lower alkoxycarbonyl and aminocarbonyl, or wherein the two substituents on nitrogen form together with the nitrogen heterocyclyl; optionally substituted alkenyl, optionally substituted alkinyl, cycloalkyl, aryl, heteroaryl, heterocyclyl, hydroxy, lower alkoxy, halo-lower alkoxy, lower alkoxy-lower alkoxy, cycloalkyl-lower alkoxy, aryloxy, aryl-lower alkoxy, aryloxy-lower alkoxy, heteroaryloxy, heteroaryl-lower alkoxy, heteroaryloxy-lower alkoxy, optionally substituted alkenyloxy, optionally substituted alkinyloxy, cycloalkyloxy, heterocyclyloxy, hydroxysulfonyloxy; alkyl mercapto, hydroxysulfinyl, alkylsulfinyl, halo-lower alkylsulfinyl, hydroxysulfonyl, alkylsulfonyl, arylsulfonyl, heteroarylsulfonyl; aminosulfonyl wherein amino is unsubstituted or substituted by one or two substituents selected from lower alkyl, cycloalkyl-lower alkyl, hydroxy-lower alkyl, lower alkoxy-lower alkyl, cycloalkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; amino optionally substituted by one or two substituents selected from lower alkyl, cycloalkyl-lower alkyl, hydroxy-lower alkyl, lower alkoxy-lower alkyl, di-lower alkylamino-lower alkyl, cycloalkyl, optionally substituted phenyl-lower alkyl and optionally substituted heteroaryl-lower alkyl, or by one substituent optionally substituted phenyl, optionally substituted heteroaryl, alkylcarbonyl, optionally substituted phenylcarbonyl, optionally substituted pyridylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; carboxymethylamino or lower alkoxycarbonylmethylamino substituted at the methyl group such that the resulting substituent corresponds to one of the 20 naturally occurring standard amino acids, aminomethylcarbonylamino substituted at the methyl group such that the resulting acyl group corresponds to one of the 20 naturally occurring standard amino acids; lower alkylcarbonyl, halo-lower alkylcarbonyl, optionally substituted phenylcarbonyl, optionally substituted heteroarylcarbonyl, carboxy, lower alkoxycarbonyl, lower alkoxy-lower alkoxycarbonyl; aminocarbonyl wherein amino is unsubstituted or substituted by one hydroxy or amino group or one or two substituents selected from lower alkyl, cycloalkyl-lower alkyl, hydroxy-lower alkyl, lower alkoxy-lower alkyl, cycloalkyl, optionally substituted phenyl-lower alkyl and optionally substituted heteroaryl-lower alkyl, or wherein the two substituents on nitrogen form together with the nitrogen heterocyclyl; cyano, halogen, and nitro; and wherein two substituents in ortho-position to each other can form a 5-, 6- or 7-membered carbocyclic or heterocyclic ring containing one, two or three oxygen atoms, one or two nitrogen atoms and/or one sulfur atom, wherein the nitrogen atoms are optionally substituted by lower alkyl, lower alkoxy-lower alkyl or lower alkylcarbonyl.

In particular, the substituents may be independently selected from lower alkyl, halo-lower alkyl, hydroxy-lower alkyl, lower alkoxy-lower alkyl, optionally substituted alkenyl, optionally substituted alkinyl, cyclohexyl, cyclopropyl, aryl, heteroaryl, heterocyclyl, hydroxy, lower alkoxy, halo-lower alkoxy, lower alkoxy-lower alkoxy, cycloalkyloxy, phenoxy, hydroxysulfonyloxy; alkylmercapto, hydroxysulfinyl, alkylsulfinyl, halo-lower alkylsulfinyl, hydroxysulfonyl, alkylsulfonyl, arylsulfonyl, heteroarylsulfonyl; aminosulfonyl wherein amino is unsubstituted or substituted by one or two substituents selected from lower alkyl, cycloalkyl-lower alkyl, hydroxy-lower alkyl, lower alkoxy-lower alkyl and optionally substituted phenyl-lower alkyl, or wherein the two substituents on nitrogen form together with the nitrogen heterocyclyl; amino optionally substituted by one or two substituents selected from lower alkyl, cycloalkyl-lower alkyl, hydroxy-lower alkyl, lower alkoxy-lower alkyl, di-lower alkylamino-lower alkyl, cycloalkyl, or by one substituent optionally substituted phenyl, optionally substituted heteroaryl, alkylcarbonyl, optionally substituted phenylcarbonyl, optionally substituted pyridylcarbonyl, alkoxycarbonyl or aminocarbonyl, or wherein the two substituents on nitrogen form together with the nitrogen heterocyclyl; carboxymethylamino or lower alkoxycarbonylmethylamino substituted at the methyl group such that the resulting substituent corresponds to one of the 20 naturally occurring standard amino acids, aminomethylcarbonylamino substituted at the methyl group such that the resulting acyl group corresponds to one of the 20 naturally occurring standard amino acids; lower alkylcarbonyl, halo-lower alkylcarbonyl, carboxy, lower alkoxycarbonyl, lower alkoxy-lower alkoxycarbonyl; aminocarbonyl wherein amino is unsubstituted or substituted by one hydroxy or amino group or one or two substituents selected from lower alkyl, hydroxy-lower alkyl, lower alkoxy-lower alkyl, optionally substituted phenyl-lower alkyl and optionally substituted heteroaryl-lower alkyl, or wherein the two substituents on nitrogen form together with the nitrogen heterocyclyl; cyano, halogen, and nitro; and wherein two substituents in ortho-position to each other can form a 5- or 6-membered heterocyclic ring containing one or two oxygen atoms and/or one or two nitrogen atoms, wherein the nitrogen atoms are optionally substituted by lower alkyl, lower alkoxy-lower alkyl or lower alkylcarbonyl.

In optionally substituted phenyl, substituents are preferably lower alkyl, halo-lower alkyl, lower alkoxy-lower alkyl, amino-lower alkyl, acylamino-lower alkyl, cyclopropyl, hydroxy, lower alkoxy, halo-lower alkoxy, lower alkoxy-lower alkoxy, methylenedioxy, hydroxy-sulfonyloxy, carboxy, lower alkoxycarbonyl, aminocarbonyl, hydroxylaminocarbonyl, tetrazolyl, hydroxysulfonyl, aminosulfonyl, halo, cyano or nitro, in particular lower alkoxy, amino-lower alkyl, acylamino-lower alkyl, carboxy, lower alkoxycarbonyl, aminocarbonyl, hydroxylaminocarbonyl, tetrazolyl, or aminosulfonyl.

Heteroaryl represents an aromatic group containing at least one heteroatom selected from nitrogen, oxygen and sulfur, and is mono- or bicyclic, optionally carrying substituents. Monocyclic heteroaryl includes 5 or 6 membered heteroaryl groups containing 1, 2, 3 or 4 heteroatoms selected from nitrogen, sulfur and oxygen. Bicyclic heteroaryl includes 9 or 10 membered fused-ring heteroaryl groups. Examples of heteroaryl include pyrrolyl, thienyl, furyl, pyrazolyl, imidazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, and benzo or pyridazo fused derivatives of such monocyclic heteroaryl groups, such as indolyl, benzimidazolyl, benzofuryl, quinolinyl, isoquinolinyl, quinazolinyl, pyrrolopyridine, imidazopyridine, or purinyl, all optionally substituted. Preferably, heteroaryl is pyridyl, pyrimdinyl, pyrazinyl, pyridazinyl, thienyl, pyrazolyl, imidazolyl, thiazolyl, oxadiazolyl, triazolyl, oxazolyl, isoxazolyl, isothiazolyl, pyrrolyl, indolyl, pyrrolopyridine or imidazopyridine; in particular pyridyl, pyrimidinyl, pyrazinyl, pyridazinyl, pyrazolyl, imidazolyl, thiazolyl, oxadiazolyl, triazolyl, indolyl, pyrrolopyridine or imidazopyridine.

The term "heteroaryl carrying substituents" stands for heteroaryl substituted by up to three substituents independently selected from lower alkyl, halo-lower alkyl, cycloalkyl-lower alkyl, hydroxy-lower alkyl, lower alkoxy-lower alkyl, aryloxy-lower alkyl, heteroaryloxy-lower alkyl, lower alkoxy-lower alkoxy-lower alkyl; aminoalkyl, wherein amino is unsubstituted or substituted by one or two substituents selected from lower alkyl, hydroxy-lower alkyl, alkoxy-lower alkyl, amino-lower alkyl, alkylcarbonyl, alkoxycarbonyl, amino-lower alkoxycarbonyl, lower alkoxy-lower alkoxycarbonyl and aminocarbonyl; optionally substituted alkenyl, optionally substituted alkinyl, cycloalkyl; aryl, heteroaryl, arylalkyl or heteroarylalkyl, wherein aryl or heteroaryl are unsubstituted or substituted by up to three substituents selected from lower alkyl, halo-lower alkyl, lower alkoxy, halogen, amino, cyano and nitro; hydroxy, lower alkoxy, halo-lower alkoxy, lower alkoxy-lower alkoxy, cycloalkyloxy, cycloalkyl-lower alkoxy, aryloxy, aryl-lower alkoxy, heteroaryloxy, heteroaryl-lower alkoxy, alkenyloxy, alkinyloxy, alkylmercapto, alkylsulfinyl, halo-lower alkylsulfinyl, alkylsulfonyl, arylsulfonyl, heteroarylsulfonyl, aminosulfonyl wherein amino is unsubstituted or substituted by one or two substituents selected from lower alkyl, cycloalkyl-lower alkyl, hydroxy-lower alkyl, lower alkoxy-lower alkyl, cycloalkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; amino optionally substituted by one or two substituents selected from lower alkyl, cycloalkyl-lower alkyl, hydroxy-lower alkyl, lower alkoxy-lower alkyl, di-lower alkylamino-lower alkyl, cycloalkyl, optionally substituted phenyl, optionally substituted phenyl-lower alkyl, optionally substituted heteroaryl, optionally substituted heteroaryl-lower alkyl, alkylcarbonyl, alkoxycarbonyl or aminocarbonyl, and wherein alkyl or lower alkyl in each case may be substituted by halogen, lower alkoxy, aryl, heteroaryl or optionally substituted amino, or wherein the two substituents on nitrogen form together with the nitrogen heterocyclyl; lower alkylcarbonyl, halo-lower alkylcarbonyl, optionally substituted phenylcarbonyl, carboxy, lower alkoxycarbonyl, lower alkoxy-lower alkoxycarbonyl; aminocarbonyl wherein amino is unsubstituted or substituted by one hydroxy or amino group or one or two substituents selected from lower alkyl, cycloalkyl-lower alkyl, hydroxy-lower alkyl, lower alkoxy-lower alkyl, cycloalkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; cyano, halogen, and nitro.

In particular, the substituents on heteroaryl may be independently selected from lower alkyl, halo-lower alkyl, cycloalkyl-lower alkyl, lower alkoxy-lower alkyl, lower alkoxy-lower alkoxy-lower alkyl, optionally substituted alkenyl, optionally substituted alkinyl, cycloalkyl, aryl, heteroaryl, hydroxy, lower alkoxy, cycloalkyloxy, alkenyloxy, alkinyloxy, alkyl-mercapto, alkylsulfinyl, halo-lower alkylsulfinyl, alkylsulfonyl, arylsulfonyl, aminosulfonyl wherein amino is unsubstituted or substituted by one or two substituents selected from lower alkyl, cycloalkyl-lower alkyl, hydroxy-lower alkyl, lower alkoxy-lower alkyl, cycloalkyl, optionally substituted phenyl, optionally substituted phenyl-lower alkyl, optionally substituted heteroaryl and optionally substituted heteroaryl-lower alkyl, or wherein the two substituents on nitrogen form together with the nitrogen heterocyclyl; amino optionally substituted by one or two substituents selected from lower alkyl, cycloalkyl-lower alkyl, hydroxy-lower alkyl, lower alkoxy-lower alkyl, di-lower alkylamino-lower alkyl, cycloalkyl, alkylcarbonyl, alkoxycarbonyl or aminocarbonyl, and wherein alkyl or lower alkyl in each case may be substituted by lower alkoxy or optionally substituted amino, or wherein the two substituents on nitrogen form together with the nitrogen heterocyclyl; lower alkyl-carbonyl, halo-lower alkylcarbonyl, carboxy, lower alkoxycarbonyl, lower alkoxy-lower alkoxycarbonyl; aminocarbonyl wherein amino is unsubstituted or substituted by one hydroxy or amino group or one or two substituents selected from lower alkyl, cycloalkyl-lower alkyl, hydroxy-lower alkyl, lower alkoxy-lower alkyl or cycloalkyl, or wherein the two substituents on nitrogen form together with the nitrogen heterocyclyl; cyano, halogen, and nitro.

In optionally substituted heteroaryl, substituents are preferably lower alkyl, halo-lower alkyl, lower alkoxy-lower alkyl, hydroxy, lower alkoxy, halo-lower alkoxy, lower alkoxy-lower alkoxy, methylenedioxy, carboxy, lower alkoxycarbonyl, aminocarbonyl, hydroxylaminocarbonyl, tetrazolyl, aminosulfonyl, halo, cyano or nitro.

Alkenyl contains one or more, e.g. two or three, double bonds, and is preferably lower alkenyl, such as 1- or 2-butenyl, 1-propenyl, allyl or vinyl.

Alkinyl is preferably lower alkinyl, such as propargyl or acetylenyl.

In optionally substituted alkenyl or alkinyl, substituents are preferably lower alkyl, lower alkoxy, halo, optionally substituted aryl or optionally substituted heteroaryl, and are connected with a saturated or unsaturated carbon atom of alkenyl or alkinyl.

Heterocyclyl designates preferably a saturated, partially saturated or unsaturated, mono- or bicyclic ring containing 4-10 atoms comprising one, two or three heteroatoms selected from nitrogen, oxygen and sulfur, which may, unless otherwise specified, be carbon or nitrogen linked, wherein a ring nitrogen atom may optionally be substituted by a group selected from lower alkyl, amino-lower alkyl, aryl, aryl-lower alkyl and acyl, and a ring carbon atom may be substituted by lower alkyl, amino-lower alkyl, aryl, aryl-lower alkyl, heteroaryl, lower alkoxy, hydroxy or oxo, or which may be fused with an optionally substituted benzo ring. Substituents considered for substituted benzo are those mentioned above for optionally substituted aryl. Examples of heterocyclyl are pyrrolidinyl, oxazolidinyl, thiazolidinyl, piperidinyl, morpholinyl, piperazinyl, dioxolanyl, tetrahydro-furanyl and tetrahydropyranyl, and optionally substituted benzo fused derivatives of such monocyclic heterocyclyl, for example indolinyl, benzoxazolidinyl, benzothiazolidinyl, tetrahydroquinolinyl, and benzodihydrofuryl.

Acyl designates, for example, alkylcarbonyl, cycloalkylcarbonyl, arylcarbonyl, aryl-lower alkylcarbonyl, or heteroarylcarbonyl. Lower acyl is preferably lower alkylcarbonyl, in particular propionyl or acetyl.

Hydroxyalkyl is especially hydroxy-lower alkyl, preferably hydroxymethyl, 2-hydroxyethyl or 2-hydroxy-2-propyl.

Cyanoalkyl designates preferably cyanomethyl and cyanoethyl.

Haloalkyl is preferably fluoroalkyl, especially trifluoromethyl, 3,3,3-trifluoroethyl or pentafluoroethyl.

Halogen is fluorine, chlorine, bromine, or iodine.

Lower alkoxy is especially methoxy, ethoxy, isopropyloxy, or tert-butyloxy.

Arylalkyl includes aryl and alkyl as defined hereinbefore, and is e.g. benzyl, 1-phenethyl or 2-phenethyl.

Heteroarylalkyl includes heteroaryl and alkyl as defined hereinbefore, and is e.g. 2-, 3- or 4-pyridylmethyl, 1- or 2-pyrrolylmethyl, 1-pyrazolylmethyl, 1-imidazolylmethyl, 2-(1-imidazolyl)ethyl or 3-(1-imidazolyl)propyl.

In substituted amino, the substituents are preferably those mentioned as substituents hereinbefore. In particular, substituted amino is alkylamino, dialkylamino, optionally substituted arylamino, optionally substituted arylalkylamino, lower alkylcarbonylamino, benzoylamino, pyridylcarbonylamino, lower alkoxycarbonylamino or optionally substituted aminocarbonylamino.

Particular salts considered are those replacing the hydrogen atoms of the sulfate group and the carboxylic acid function. Suitable cations are, e.g., sodium, potassium, calcium, magnesium or ammonium cations, or also cations derived by protonation from primary, secondary or tertiary amines containing, for example, lower alkyl, hydroxy-lower alkyl or hydroxy-lower alkoxy-lower alkyl groups, e.g., 2-hydroxyethylammonium, 2-(2-hydroxyethoxy)ethyldimethylammonium, diethylammonium, di(2-hydroxyethyl)ammonium, trimethylammonium, triethylammonium, 2-hydroxyethyldimethylammonium, or di(2-hydroxyethyl) methylammonium, also from correspondingly substituted cyclic secondary and tertiary amines, e.g., N-methylpyrrolidinium, N-methylpiperidinium, N-methyl-morpholinium, N-2-hydroxyethylpyrrolidinium, N-2-hydroxyethylpiperidinium, or N-2-hydroxyethylmorpholinium, and the like.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, and vice versa, as appropriate and expedient.

Preferably Z is unsubstituted or substituted phenyl.

In particular, the invention refers to compounds of formula (I) or (II), wherein Z is optionally substituted phenyl.

Preferred substituents considered for Z with the meaning of the mentioned aryl groups, e.g. phenyl, are lower alkyl, halo-lower alkyl, hydroxy-lower alkyl, lower alkoxy-lower alkyl, amino-lower alkyl, lower alkanecarbonylamino-lower alkyl, mercapto-lower alkane-carbonylamino-lower alkyl, optionally substituted alkenyl, optionally substituted alkinyl, cyclohexyl, cyclopropyl, aryl, heteroaryl, heterocyclyl, hydroxy, lower alkoxy, halo-lower alkoxy, lower alkoxy-lower alkoxy, cycloalkyloxy, hydroxysulfonyloxy; mercapto, alkylmercapto, hydroxysulfinyl, alkylsulfinyl, halo-lower alkylsulfinyl, hydroxysulfonyl, alkylsulfonyl, arylsulfonyl, heteroarylsulfonyl, aminosulfonyl wherein amino is unsubstituted or substituted by one or two substituents selected from lower alkyl, cycloalkyl-lower alkyl, hydroxy-lower alkyl, lower alkoxy-lower alkyl, optionally substituted phenyl-lower alkyl and optionally substituted heteroaryl-lower alkyl, or wherein the two substituents on nitrogen form together with the nitrogen heterocyclyl; amino optionally substituted by one or two substituents selected from lower alkyl, cycloalkyl-lower alkyl, hydroxy-lower alkyl, lower alkoxy-lower alkyl and di-lower alkylamino-lower alkyl, or by one substituent cycloalkyl, optionally substituted phenyl, optionally substituted heteroaryl, alkylcarbonyl, optionally substituted phenylcarbonyl, optionally substituted pyridylcarbonyl, alkoxycarbonyl or aminocarbonyl, or wherein the two substituents on nitrogen form together with the nitrogen heterocyclyl; carboxymethylamino or lower alkoxycarbonylmethylamino substituted at the methyl group such that the resulting substituent corresponds to one of the 20 naturally occurring standard amino acids, aminomethylcarbonylamino substituted at the methyl group such that the resulting acyl group corresponds to one of the 20 naturally occurring standard amino acids; lower alkylcarbonyl, halo-lower alkylcarbonyl, carboxy, lower alkoxycarbonyl, lower alkoxy-lower alkoxycarbonyl; aminocarbonyl wherein amino is unsubstituted or substituted by one hydroxy or amino group or one or two substituents selected from lower alkyl, hydroxy-lower alkyl, lower alkoxy-lower alkyl, optionally substituted phenyl-lower alkyl and optionally substituted heteroaryl-lower alkyl, or wherein the two substituents on nitrogen form together with the nitrogen heterocyclyl; cyano, halogen, and nitro; and wherein two substituents in ortho-position to each other can form a 5- or 6-membered heterocyclic ring containing one or two oxygen atoms and/or one or two nitrogen atoms, wherein the nitrogen atoms are optionally substituted by lower alkyl, lower alkoxy-lower alkyl or lower alkylcarbonyl.

Particularly preferred Z is p-methoxyphenyl, 4-(2-aminoethyl)phenyl or 4-(2-(4-mercaptobutanoylamino)ethyl)phenyl.

In polymers comprising a multitude of substituents of formula (I) and/or formula (II), a particular linker Z is (bifunctional) aryl, heteroaryl, aryl-lower alkyl, arylcarbonyl, or heteroarylmethyl, wherein aryl or heteroaryl is substituted by $-(CH_2)_2NH(C{=}O)(CH_2)_3S-CH_2-(C{=}O)-$ connecting to the polymer with aminoalkyl side chains at the C=O function.

More particularly linker Z is phenyl substituted by $-(CH_2)_2NH(C{=}O)(CH_2)_3S-CH_2-(C{=}O)-$ connecting to the polymer with aminoalkyl side chains at the C=O function.

A preferred polymer in polymers comprising a multitude of substituents of formula (I) and/or formula (II) is polylysine, in particular poly-L-lysine.

Preferably the molecular weight of the polylysine is 1,000 to 300,000 kD, preferably 10,000 to 100,000 kD. Particularly preferred is a molecular weight of approximately 50,000 kD, 125,000 kD or 200,000 kD. Most preferred is a molecular weight of approximately 50,000 kD.

In particular the invention relates to such polymers wherein the relative loading of polymer backbone with the disaccharide of formula (I) and/or (II) is 10-80%, meaning that 10-80% of all lysine side chains in the polymer are coupled/reacted with a linker carrying a disaccharide, the remaining amino functions being capped. Preferably the loading of the polymer is 30-60%, more preferably 40-50%.

In a particular embodiment, the sulfated minimal HNK-1 epitope 22 carrying a linker with a terminal sulfhydryl function was synthesized and reacted in a substochiometric amount with the activated (chloroacetylated) lysine polymer 24. The carbohydrate loading (40%) was determined by $^1H$ NMR. The starting polymer 23 had an average molecular weight (MW) of 50 kD, whereas the final polymer (25) with 40% minimal HNK-1 epitope loading had a calculated average MW of 123 kD.

The synthesized carbohydrate monomers (1 and 2) and the polymer 25 were tested in an established ELISA assay (Bühlmann Laboratories, Schonenbuch, Switzerland) applied for the diagnosis of anti-MAG neuropathy and for therapy control in clinic. The assay is used to determine serum concentration of anti-MAG IgM autoantibodies. The assay was modified to a competitive binding assay. The synthesized compounds and serum samples containing anti-MAG IgM antibodies are given into 96 well plates, coated with purified MAG from human brain. Immobilized MAG and the synthesized compounds compete for binding to the anti-MAG IgM antibodies. After a washing step MAG-bound IgM antibodies are detected with a horseradish peroxidase labeled antibody, followed by a colorimetric reaction. Successful competition of the compounds with MAG leads to a decrease in measured $OD_{450\ nm}$ (optical density), because they block the binding sites of IgM antibodies, preventing them from binding to MAG. The principle of the assay is depicted in FIG. 1. For the evaluation of the compounds, four sera from different patients (MK, DP, KH, SJ) with reported high anti-MAG IgM antibody titers were chosen. IgM antibody concentrations were determined for each serum in preliminary experiments. Serum dilutions with measured $OD_{450\ nm}$ values around 1.0 were chosen for the assay, to be able to compare the measured $IC_{50}$ values (half maximal inhibitory concentration) which are antibody concentration dependent. Serum dilutions: DP 1:2'500, KH 1:3,000, SJ 1:7,500, MK 1:23,000. The two sera that served as negative controls (dilution 1:1000) showed no binding to MAG.

Figure 2:
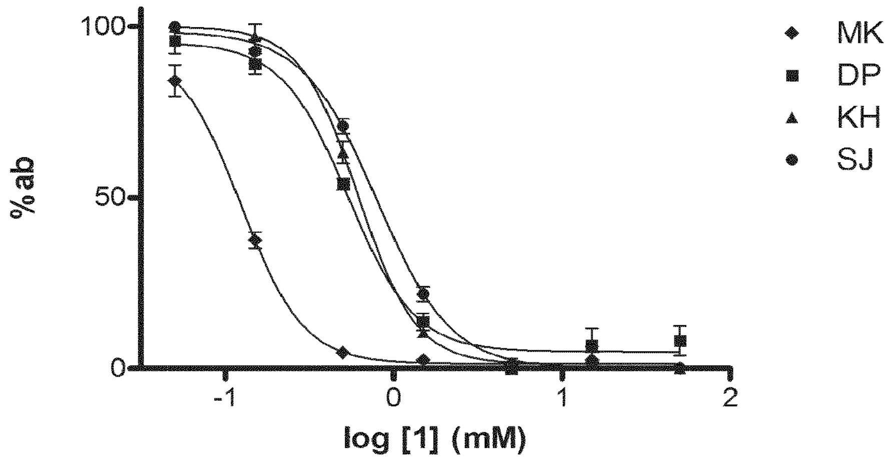
FIG. 2. Binding curves for compounds 1, 2 and 25
Figure 2:
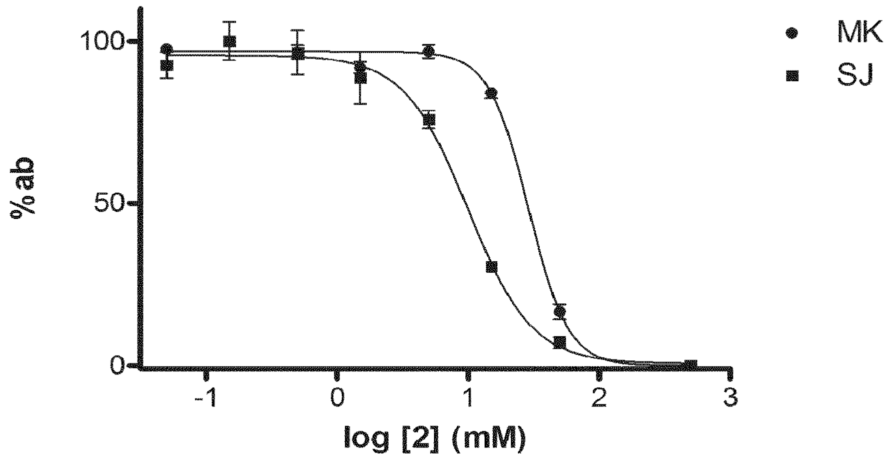
Figure 2:
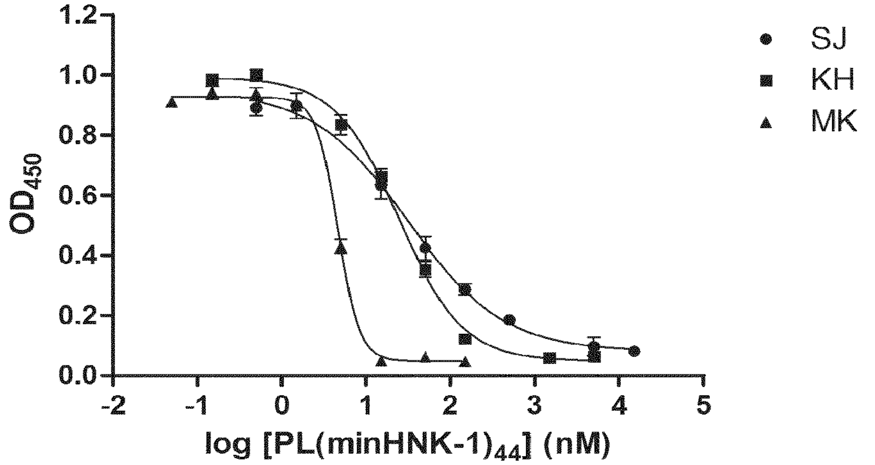
Figure 2:
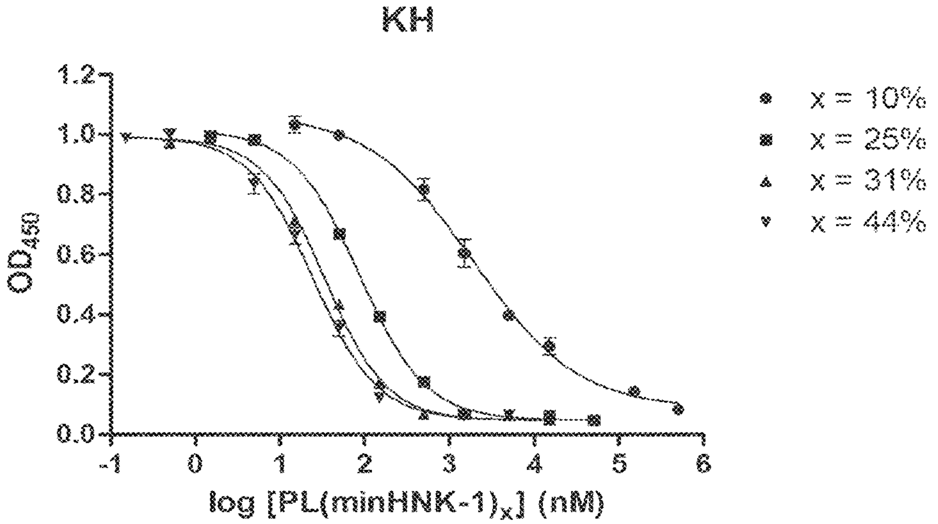
Figure 2:
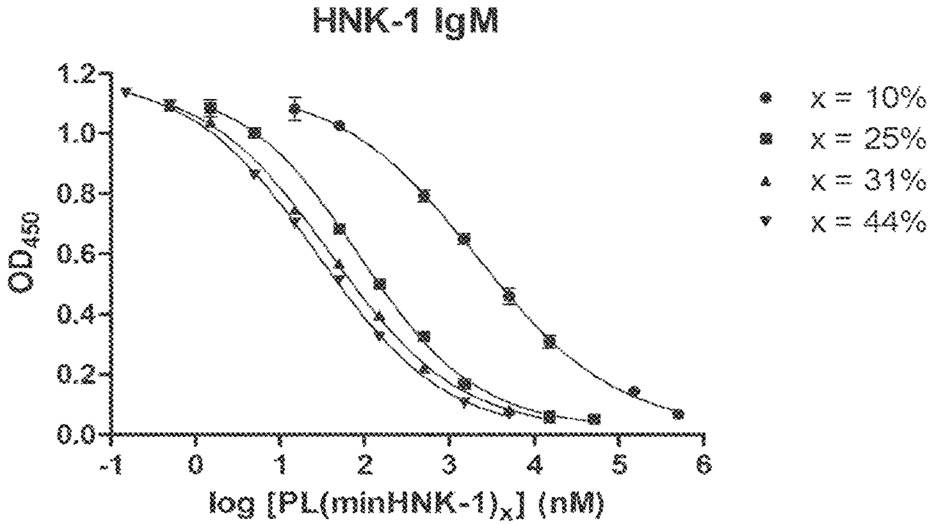

$IC_{50}$ values of compound 1 were determined for all sera. Those of compound 2 were determined for serum MK with the highest antibody affinity for 1 and for serum SJ with the lowest antibody affinity for 1. The results are shown in the Table below. The assay was repeated four times. From the received binding curves for each serum, the three best fitted were chosen and normalized for $IC_{50}$ calculation. The binding curves are shown in FIG. 2. For curve generation of compound 2 an artificially high concentration point at 500 mM with 0% antibody binding was added because even at the highest concentration of 2 (50 mM) the inhibition of antibody binding was not 100%. The $IC_{50}$ values for compound 2 are therefore to be considered as approximated values, although they changed only marginally upon addition of the high concentration point. Under the same assay conditions the carbohydrate polymer was tested with the sera KH, MK and SJ. The measurements were repeated at least three times. The three best fitted curves for each serum were chosen for $IC_{50}$ calculation. The non-normalized binding curves are shown in FIG. 2.

TABLE $IC_{50}$ values of compounds 1, 2 and the minimal HNK-1 polymer (25) for the four patient sera including standard deviations.

| Serum | Compound 1 $IC_{50}$ (μM) | Compound 2 $IC_{50}$ (mM) | Polymer (25) $IC_{50}$ (nM) |
|---|---|---|---|
| MK | 124.2 ± 9.5 | 29.0 ± 0.5 | 2.5 ± 0.1 |
| DP | 536.1 ± 23.5 | n.d. | n.d. |
| KH | 614.2 ± 20.1 | n.d. | 18.3 ± 2.2 |
| SJ | 793.1 ± 24.0 | 10.0 ± 1.0 | 14.8 ± 0.6 |

The data from the biological evaluation of 1 and 2 clearly show different affinities of the IgM antibodies of each serum to the synthesized disaccharides. Disaccharide 1 shows a superior binding affinity towards the IgM antibodies when compared to disaccharide 2, which lacks the sulfate moiety. The sulfate group seems to be essential to the synthesized minimal HNK-1 epitope for antibody binding. Nevertheless, it is not equally important for all sera. Serum MK showed high requirement for the sulfate with an approximately 230-fold weaker binding to the unsulfated disaccharide. Serum SJ on the other hand showed only 12.6-fold lower binding affinity to the unsulfated disaccharide. The carboxyl group of GlcA seems to be more important to this serum.

For all IgM antibodies, the sulfate moiety is required for binding in the μM range. It is surprising that the sulfated minimal HNK-1 epitope is capable of inhibiting the antibody binding to MAG in the μM concentration range. This suggests the possibility that the terminal aromatic moiety of the disaccharide is involved in binding, as if mimicking the third sugar (GlcNAc) of the HNK-1 epitope. The aromatic ring could undergo cation-Tr interaction or π-π stacking.

The causal relationship between anti-MAG autoantibodies and neuropathy development in anti-MAG neuropathy patients is widely accepted today (M.C. Dalakas, Current Treatment Options in Neurology 2010, 12:71-83). The antigenic determinant for these antibodies is the HNK-1 carbohydrate epitope, the trisaccharide $SO_4$-3-GlcA(β1-3)Gal(β1-4)GlcNAc—OH which is also recognized by the HNK-1 antibody.

According to the present invention it is shown that carbohydrate ligands blocking the IgM antibody binding sites prevent the antibody binding to MAG and other myelin targets.

It is shown that disaccharide ligands of formula (I) and (II), minimal HNK-1 carbohydrate epitopes, which are much easier to prepare than larger carbohydrates, retain affinity to the IgM antibodies, and are useful for diagnostic and therapeutic purposes.

Compounds related to substance 1 and 2 are known in the state of the art, but not such compounds containing arylic aglycons. Aromatic residues Z take part in the binding process to the anti-MAG IgM antibodies and therefore bestow a substantial benefit on compounds such as (I) and/or (II) with arylic aglycons.

In the case of the sulfated structure (I) an ethylamine substituted derivative of a pentasaccharide is published (A. V. Kornilov, Carbohydrate Research 2000, 329:717-730). In the case of structure (II) the unsubstituted derivative (R═H) and derivatives with common alkyl residues are published. In addition to the presently claimed aryl substitution, such as para-methoxyphenyl, the approach to present this epitope in multiple copies on a suitable polymer is novel.

Natural carbohydrates generally display low binding affinity for their binding partners. In biological systems sufficient affinity is often achieved by multivalent presentation of carbohydrates, as well as oligovalent presentation of carbohydrate recognizing domains (CRDs) of carbohydrate binding proteins (B. Ernst and J. L. Magnani, Nature Reviews Drug Discovery 2009, 8:661-677). This is also the case for the binding of IgM antibodies to MAG: MAG presents up to eight HNK-1 epitopes on its extracellular domains.

In a particularly preferred embodiment, the invention relates to polymers comprising a multitude of substituents of formula (I) and/or formula (II), wherein the polymer is poly-L-lysine and Z is a bifunctional linker connecting said substituent to the polymer backbone.

Poly-L-lysine is biodegradable and therefore suitable for therapeutical application. The exemplified minimal HNK-1 polymer shows a massive increase in binding affinity toward the pathogenic IgM antibodies. The inhibitory activity, now being in the low nM range, is increased by a factor of at least 34,000 compared to the monomer (serum KH). The affinity increase obtained for serum MK and SJ was approximately 50,000 (see Table above). These findings clearly indicate the multivalent nature of the antigen-antibody interaction.

The exemplified minimal HNK-1 polymer serves as substitute antigen for purified human brain MAG currently used in a diagnostic ELISA assay for the detection of anti-MAG IgM antibodies.

The compounds of the invention have valuable pharmacological properties. The invention also relates to compounds as defined hereinbefore for use as medicaments. A compound according to the invention shows prophylactic and therapeutic efficacy especially against anti-MAG neuropathy.

A compound of formula (I) or (II), or polymers comprising these, can be administered alone or in combination with one or more other therapeutic agents, possible combination therapy taking the form of fixed combinations, or the administration of a compound of the invention and one or more other therapeutic agents being staggered or given independently of one another, or the combined administration of fixed combinations and one or more other therapeutic agents.

Therapeutic agents for possible combination are especially immunosuppressive agents. Examples are purine analogues such as fludarabine and/or cladribine, furthermore the chimeric monoclonal antibody rituximab (A. J. Steck et al., Current Opinion in Neurology 2006, 19:458-463).

In another particular embodiment, the invention relates to the use of the compounds of the invention in a diagnostic assay for anti-MAG neuropathy. In particular, the invention relates to kits comprising the compounds of formula (I) or (II) as defined above, and also polymers of the invention comprising such compounds as substituents.

The present invention relates to a method of diagnosis of anti-MAG neuropathy, wherein the level of IgM against MAG is determined in a body fluid sample, e.g. serum, and a high level is indicative of the development and the severity of anti-MAG neuropathy.

Other body fluids than serum useful for determination of IgM against MAG are, e.g., whole blood, cerebrospinal fluid or extracts from solid tissue.

Any known method may be used for the determination of the level of IgM against MAG in body fluids. Methods considered are, e.g., ELISA, RIA, EIA, or microarray analysis.

A preferred method for the determination of IgM against MAG in human body fluids, e.g. in serum, is an ELISA. In such an embodiment, microtiter plates are coated with compounds of formula (I) or (II), or preferably polymers of the invention comprising such compounds as substituents. The plates are then blocked and the sample or a standard solution is loaded. After incubation, an anti-IgM antibody is applied, e.g. an anti-IgM antibody directly conjugated with a suitable label, e.g. with an enzyme for chromogenic detection. Alternatively, a polyclonal rabbit (or mouse) anti-IgM antibody is added. A second antibody detecting the particular type of the anti-IgM antibody, e.g. an anti-rabbit (or anti-mouse) antibody, conjugated with a suitable label, e.g. the enzyme for chromogenic detection as above, is then added. Finally the plate is developed with a substrate for the label in order to detect and quantify the label, being a measure for the presence and amount of IgM against MAG. If the label is an enzyme for chromogenic detection, the substrate is a colour-generating substrate of the conjugated enzyme. The colour reaction is then detected in a microplate reader and compared to standards.

It is also possible to use antibody fragments. Suitable labels are chromogenic labels, i.e. enzymes which can be used to convert a substrate to a detectable colored or fluorescent compound, spectroscopic labels, e.g. fluorescent labels or labels presenting a visible color, affinity labels which may be developed by a further compound specific for the label and allowing easy detection and quantification, or any other label used in standard ELISA.

Other preferred methods of IgM against MAG detection are radioimmunoassay or competitive immunoassay and chemiluminescence detection on automated commercial analytical robots. Microparticle enhanced fluorescence, fluorescence polarized methodologies, or mass spectrometry may also be used. Detection devices, e.g. microarrays, are useful components as readout systems for IgM against MAG.

In a further embodiment the invention relates to a kit suitable for an assay as described above, in particular an ELISA, comprising compounds of formula (I) or (II), or polymers comprising such compounds as substituents. The kits further contain anti-IgM antibodies (or anti-IgM antibody fragments) carrying a suitable label, or anti-IgM antibodies and second antibodies carrying such a suitable label, and reagents or equipment to detect the label, e.g. reagents reacting with enzymes used as labels and indicating the presence of such a label by a colour formation or fluorescence, standard equipment, such as microtiter plates, pipettes and the like, standard solutions and wash solutions.

The ELISA can be also designed in a way that patient blood or serum samples are used for the coating of microtiter plates with the subsequent detection of anti-MAG antibodies with labelled compounds of formula (I) or (II), or labelled polymers comprising such compounds as substituents. The label is either directly detectable or indirectly detectable via an antibody.

The polymer carrying compounds of formula (I) or (II) of the invention binds to the pathogenic anti-MAG IgM antibodies and potentially downregulates the anti-MAG IgM antibody production. It allows an antigen-specific treatment for anti-MAG neuropathy patients.

Furthermore the invention relates to a pharmaceutical composition comprising a compound of formula (I) or (II), or a polymer carrying compounds of formula (I) or (II) of the invention.

Pharmaceutical compositions for parenteral administration, such as subcutaneous, intravenous, intrahepatic or intramuscular administration, to warm-blooded animals, especially humans, are considered. The compositions comprise the active ingredient(s) alone or, preferably, together with a pharmaceutically acceptable carrier. The dosage of the active ingredient(s) depends upon the age, weight, and individual condition of the patient, the individual pharmacokinetic data, and the mode of administration.

For parenteral administration preference is given to the use of suspensions or dispersions of the carbohydrate polymer of the invention, especially isotonic aqueous dispersions or suspensions which, for example, can be made up shortly before use. The pharmaceutical compositions may be sterilized and/or may comprise excipients, for example preservatives, stabilizers, wetting agents and/or emulsifiers, solubilizers, viscosity-increasing agents, salts for regulating osmotic pressure and/or buffers and are prepared in a manner known per se, for example by means of conventional dissolving and lyophilizing processes.

Suitable carriers for enteral administration, such as nasal, buccal, rectal or oral administration, are especially fillers, such as sugars, for example lactose, saccharose, mannitol or sorbitol, cellulose preparations, and/or calcium phosphates, for example tricalcium phosphate or calcium hydrogen phosphate, and also binders, such as starches, for example corn, wheat, rice or potato starch, methylcellulose, hydroxypropyl methylcellulose, sodium carboxymethylcellulose, and/or polyvinylpyrrolidone, and/or, if desired, disintegrators, such as the above-mentioned starches, also carboxymethyl starch, crosslinked polyvinylpyrrolidone, alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Tablet cores can be provided with suitable, optionally enteric, coatings through the use of, inter alia, concentrated sugar solutions which may comprise gum arabic, talc, polyvinyl-pyrrolidone, polyethylene glycol and/or titanium dioxide, or coating solutions in suitable organic solvents or solvent mixtures, or, for the preparation of enteric coatings, solutions of suitable cellulose preparations, such as acetyl-cellulose phthalate or hydroxypropyl-methylcellulose phthalate. Dyes or pigments may be added to the tablets or tablet coatings, for example for identification purposes or to indicate different doses of active ingredient(s).

Pharmaceutical compositions for oral administration also include hard capsules consisting of gelatin, and also soft, sealed capsules consisting of gelatin and a plasticizer, such as glycerol or sorbitol. The hard capsules may contain the active ingredient in the form of granules, for example in admixture with fillers, such as corn starch, binders, and/or glidants, such as talc or magnesium stearate, and optionally stabilizers. In soft capsules, the active ingredient is preferably dissolved or suspended in suitable liquid excipients, such as fatty oils, paraffin oil or liquid polyethylene glycols or fatty acid esters of ethylene or propylene glycol, to which stabilizers and detergents, for example of the polyoxyethylene sorbitan fatty acid ester type, may also be added.

Pharmaceutical compositions suitable for rectal administration are, for example, suppositories that consist of a combination of the active ingredient and a suppository base. Suitable suppository bases are, for example, natural or synthetic triglycerides, paraffin hydrocarbons, polyethylene glycols or higher alkanols.

The mentioned pharmaceutical compositions according to the invention may contain separate tablets, granules or other forms of orally acceptable formulation of the active ingredients, or may contain a mixture of active ingredients in one suitable pharmaceutical dosage form, as described above. In particular the separate orally acceptable formulations or the mixture in one suitable pharmaceutical dosage form may be slow release and controlled release pharmaceutical compositions.

The pharmaceutical compositions comprise from approximately 1% to approximately 95% active ingredient or mixture of active ingredients, single-dose administration forms comprising in the preferred embodiment from approximately 20% to approximately 90% active ingredient(s) and forms that are not of single-dose type comprising in the preferred embodiment from approximately 5% to approximately 20% active ingredient(s).

The invention also relates to the mentioned pharmaceutical compositions as medicaments in the treatment of anti-MAG neuropathy.

The present invention relates furthermore to a method of treatment of anti-MAG neuropathy, which comprises administering a composition according to the invention in a quantity effective against said disease, to a warm-blooded animal requiring such treatment. The pharmaceutical compositions can be administered prophylactically or therapeutically, preferably in an amount effective against the said diseases, to a warm-blooded animal, for example a human, requiring such treatment. In the case of an individual having a bodyweight of about 70 kg the daily dose administered is from approximately 0.01 g to approximately 5 g, preferably from approximately 0.25 g to approximately 1.5 g, of the active ingredients in a composition of the present invention.

The following Examples serve to illustrate the invention without limiting the invention in its scope.

EXAMPLES

General Methods

NMR spectra were obtained on a Bruker Avance DMX-500 (500 MHz) spectrometer.

Assignment of $^{1}H$ and $^{13}C$ NMR spectra was achieved using 2D methods (COSY and HSQC). Chemical shifts are expressed in ppm using residual $CHCl_3$, $CHD_2OD$ or HDO as references. Optical rotations were measured on a Perkin-Elmer polarimeter 341. IR spectra were recorded using a Perkin-Elmer Spectrum One FT-IR spectrometer. Electron spray ionization mass spectra (ESI-MS) were obtained on a Waters micromass ZQ. HRMS analysis was carried using an Agilent 1100 LC equipped with a photodiode array detector and a Micromass QTOF I equipped with a 4 GHz digital-time converter. Reactions were monitored by TLC using glass plates coated with silica gel 60 $F_{254}$ (Merck) and visualized by using UV light and/or by charring with mostain (a 0.02 M solution of ammonium cerium sulfate dihydrate and ammonium molybdate tetrahydrate in aq 10% $H_2SO_4$). Column chromatography was performed on silica gel (Fluka C60 40/60) or RP-18 (Merck LiChroprep® RP-18 40/60). Methanol (MeOH) was dried by refluxing with sodium methoxide and distillation. Pyridine was dried over activated molecular sieves (4 Å). Dimethylformamide (DMF) was purchased from Acros (99.8%, extra dry, over molecular sieves). Dichloromethane (DCM), toluene and hexane were dried by filtration over $Al_2O_3$ (Fluka, type 5016A basic). Molecular sieves (4 Å) were activated in vacuo at 500° C. for 1 h immediately before use. Centrifugations were carried out with an Eppendorf Centrifuge 5804 R. rt=room temperature.

The three compounds for the biological evaluation (1, 2 and 25) were synthesized according to Scheme 1 and 2. All reagents were bought from Sigma Aldrich or Acros. The GlcA-Gal disaccharides 5 were obtained by reacting the activated GlcA donor 3 (C. Coutant and J.-C. Jacquinet, J Chem Soc Perkin Trans I, 1995, 1573-1581) and the selectively protected Gal acceptor 4 (F. Belot et al., Synlett 2003, 1315-1318) with trimethylsilyl trifluoromethanesulfonate (TMSOTf) as promoter. Deprotection of the ester groups with LiOH in tetrahydrofuran (THF)/water ($H_2O$) yielded 6. Disaccharides 2 were obtained by catalytic hydrogenation. The 3'-unprotected disaccharides 7 were synthesized via a lactonization/methanolysis procedure published by A. V. Kornilov (Carbohydrate Research 2000, 329:717-730). Subsequent sulfation with the sulfate-pyridine complex ($SO_3 \cdot Py$) in N,N-dimethylformamide (DMF) gave 3-O-sulfated disaccharide 8 (65%). Final deprotection by catalytic hydrogenation followed by hydrolysis and treatment with $Na^+$ cation-exchange resin afforded the desired sulfated disaccharides 1.

For the synthesis of the carbohydrate polymer 25, the sulfated monomer 21 was prepared (Scheme 1). It contains a 4-(2-aminoethyl)phenyl aglycone instead of para-methoxyphenyl present in 1. The additional primary amino group was required for the coupling to the polylysine polymer. For its synthesis, 4-(2-azidoethyl)phenol (9) was galactosylated with the trichloroacetimidate donor 10 (R. Burkowski et al., Eur J Org Chem 2001, 2697-2705). Acceptor 9 was obtained by amine-azide interconversion (A. Titz et al., Tet. Letters 2006, 47:2383-2385) from tyrosine. Deacetylation under Zempén conditions (giving 12), followed by the formation of the 3,4-isopropylidene derivative 13, dibenzylation (results in 14), acid-catalyzed cleavage of the acetonide (gives 15) and mono-benzoylation yielded galactoside 16. For the remaining steps to the monosulfated disaccharide 21 a similar reaction sequence as already applied for the synthesis of disaccharide 1 was applied, except for the benzylation which was carried out under phase transfer catalysis using 50% aqueous NaOH/DCM and 18-crown-6 ether. The free amino group in 21 was then reacted with thiobutyrolactone and triethylamine (TEA) in DMF to give compound 22 in 59% yield, ready for coupling to the polylysine polymer.

For this purpose, the commercial polylysine polymer 23 was acylated, giving 24 in 96% yield (G. Thoma et al., J Am Chem Soc 1999, 121:5919-5929) before it was coupled to a substochiometric amount of the minimal HNK-1 epitope 22 (0.4 eq). To improve the water solubility of the glycosylated polylysine polymer, the remaining chloroacetamide groups were capped with an excess of thioglycerol. Purification by ultrafiltration (Sartorius Stedim Vivaspin 6, molecular weight cutoff, 5000) yielded glycopolymer 25 in 70% yield.

9.6 Hz, 1H, H-3), 4.46 (A, B of AB, J=11.5 Hz, 2H, $CH_2Ph$), 4.51, 4.90 (A, B of AB, J=10.5 Hz, 2H, $CH_2Ph$), 4.94 (d, J=7.8 Hz, 1H, H-1), 5.36 (d, J=7.5 Hz, 1H, H-1'), 5.44 (dd, J=7.5, 9.2 Hz, 1H, H-2'), 5.66 (t, J=9.6 Hz, 1H, H-4), 5.72-5.79 (m, 2H, H-3', H-4'), 6.76, 7.00 (AA', BB' of AA'BB', J=9.1 Hz, 4H, $C_6H_4$), 7.19-7.44, 7.47-7.51, 7.54-7.61, 7.75-7.78, 7.87-7.91, 8.03-8.08 (m, 30H, 6 $C_6H_5$); $^{13}C$ NMR (126 MHz, $CDCl_3$): δ 52.88, 55.64 (2 OMe), 69.07 (C-6), 70.01 (C-4), 70.05 (C-4'), 71.76 (C-2'), 72.17 (C-3'),

Scheme 1: Synthesis of the minimal HNK-1 epitope in sulfated (1) and unsulfated form (2)

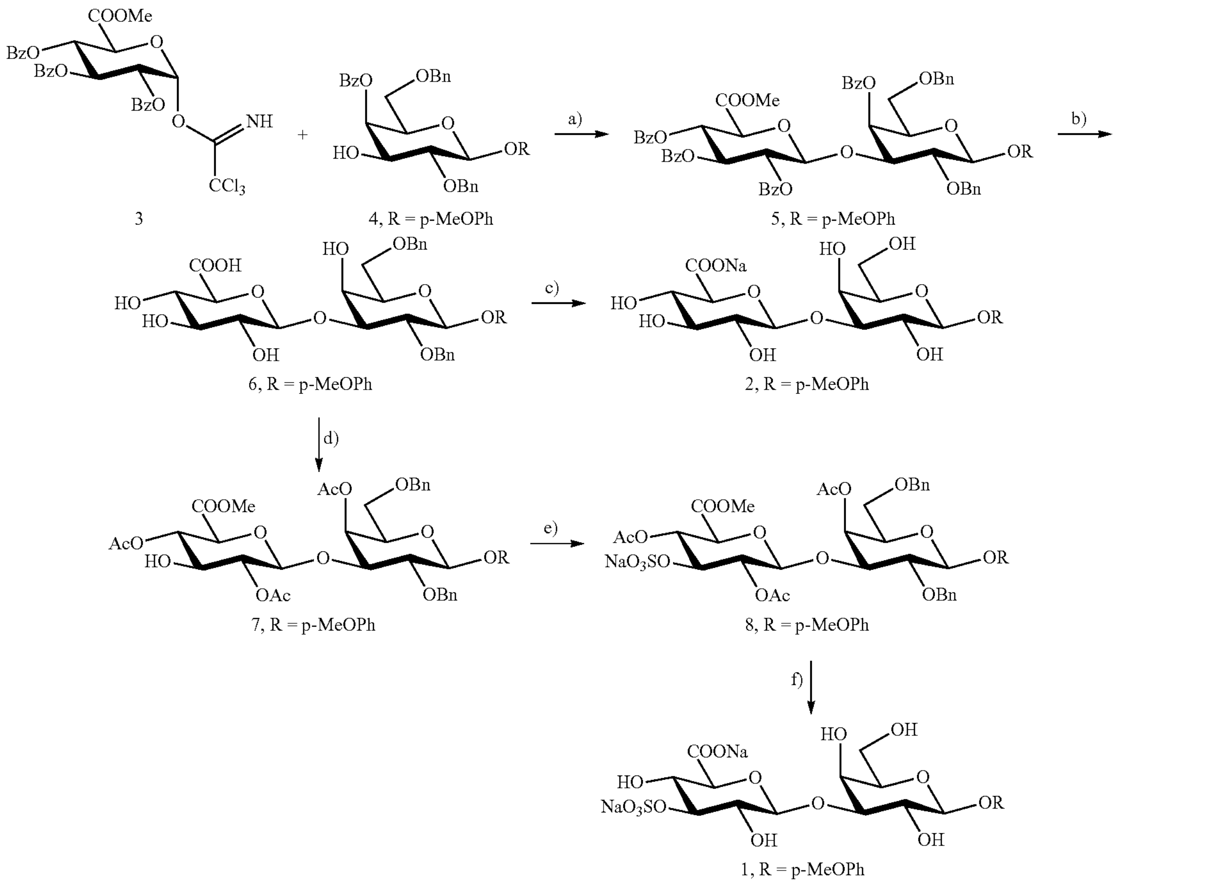

3 + 4, R = p-MeOPh → 5, R = p-MeOPh

6, R = p-MeOPh → 2, R = p-MeOPh

7, R = p-MeOPh → 8, R = p-MeOPh

1, R = p-MeOPh

Reagents and conditions: a) TMSOTf, molecular sieves 4 Å, DCM, 0° C. to rt, (81%) b) LiOH, THF/$H_2O$ (97%); c) $Pd(OH)_2/C$, $H_2$, MeOH/$H_2O$ (96%); d) $Ac_2O$, 80° C., pyr, DMAP; MeOH, anhyd AcONa (57%); e) $SO_3$•Py, DMF (65%); f) $Pd(OH)_2/C$, $H_2$, MeOH/$H_2O$, LiOH, MeOH/$H_2O$ (88%).

4-Methoxyphenyl (Methyl 2,3,4-Tri-O-Benzoyl-β-D-Glucopyranuronate)-(1→3)-4-O-Benzoyl-2,6-Di-O-Benzyl-β-D-Galactopyranoside (5).

Under argon 3 (1.12 g, 1.68 mmol), 4a (800 mg, 1.40 mmol) and activated 4 Å molecular sieves (1.2 g) were suspended in DCM (30 mL). The mixture was stirred for 1 h at rt and then cooled to 0 ° C. TMSOTf (38.1 μL, 0.21 mmol) was added dropwise. The reaction mixture was allowed to warm to rt overnight, and was then neutralized with TEA (100 μL) and concentrated. The residue was purified by chromatography (petroleum ether/EtOAc, 9:1 to 7:3) to yield 5 (1.21 g, 1.13 mmol, 81%) as a white solid.

$[\alpha]_D^{20}$+28.4 (c 1.01, $CHCl_3$); $^1H$ NMR (500 MHz, $CDCl_3$): δ 3.59 (dd, J=7.2, 10.1 Hz, 1H, H-6a), 3.65 (s, 3H, OMe), 3.69 (dd, J=4.8, 10.1 Hz, 1H, H-6b), 3.74 (s, 3H, OMe), 3.93 (dd, J=7.8, 9.5 Hz, 1H, H-2), 3.96 (dd, J=5.1, 6.9 Hz, 1H, H-5), 4.12 (d, J=9.8 Hz, 1H, H-5'), 4.20 (dd, J=3.5, 72.90 (C-5'), 73.54 (C-5), 73.72, 75.23 (2 $CH_2Ph$), 76.16 (C-3), 79.86 (C-2), 100.29 (C-1'), 102.73 (C-1), 114.57, 118.19 (4C, $C_6H_4$), 127.69, 127.78, 128.00, 128.09, 128.30, 128.37, 128.43, 128.59, 128.71, 128.89, 129.05, 129.58, 129.77, 129.82, 129.92, 130.11, 132.91, 133.08, 133.27, 133.39, 137.88, 137.90 (36C, 6 $C_6H_5$), 151.33, 155.33 (2C, $C_6H_4$), 164.45, 165.00, 165.52, 165.63, 167.15 (5 CO); ESI-MS: m/z: calcd for $C_{62}H_{56}NaO_{17}$ $[M+Na]^+$: 1095.35, found: 1095.48.

4-Methoxyphenyl (β-D-Glucopyranuronate)-(1→3)-2,6-Di-O-Benzyl-β-D-Galactopyranoside Compound 5 (810 mg, 0.76 mmol) was suspended in THF (7 mL) and the suspension was cooled to −10° C. Then 2 M aq LiOH (5 mL) was added dropwise. The reaction mixture was stirred overnight and allowed to warm to rt. The solvents were evaporated, the residue was taken up in THF/$H_2O$ (2:3, 8 mL) and treated with TFA (4 mL) for 30 min. The mixture was evaporated to dryness and the residue was purified by reversed-phase chromatography (RP-18, MeOH/water, 0:1 to 2:1) to give 6 (0.47 g, 0.73 mmol, 97%) as a white solid.

$[\alpha]_D^{20}$ −43.2 (c 1.00, MeOH); $^1$H NMR (500 MHz, $CD_3OD$): δ 3.30-3.41 (m, 2H, H-2', H-3'), 3.49 (t, J=8.9 Hz, 1 H, H-4'), 3.66 (s, 3H, OMe), 3.68 (d, J=5.9 Hz, 2H, H-6a, H-6b), 3.72 (d, J=9.7 Hz, 1 H, H-5'), 3.76 (d, J=5.9 Hz, 1 H, H-5), 3.79 (dd, J=3.3, 9.9 Hz, 1 H, H-3), 3.87 (m, 1H, H-2), 4.00 (d, J=2.7 Hz, 1H, H-4), 4.48 (s, 2H, $CH_2Ph$), 4.70 (d, J=7.4 Hz, 1 H, H-1'), 4.84 (d, J=7.7 Hz, 1H, H-1), 4.87 (s, 2H, $CH_2Ph$), 6.73, 6.97 (AA', BB' of AA'BB', J=9.0 Hz, 4H, $C_6H_4$), 7.17-7.28 (m, 8H, 2 $C_6H_5$), 7.38 (d, J=7.1 Hz, 2H, 2 $C_6H_5$); $^{13}$C NMR (126 MHz, $CD_3OD$): δ 56.10 (OMe), 70.37 (C-4), 70.72 (C-6), 73.35 (C-4'), 74.37 ($CH_2Ph$), 74.85 (C-2'), 75.00 (C-5), 76.22 (C-5'), 76.46 ($CH_2Ph$), 77.35 (C-3'), 80.11 (C-2), 82.20 (C-3), 103.87 (C-1), 105.59 (C-1'), 115.58, 119.23 (4C, $C_6H_4$), 128.66, 128.76, 128.79, 129.31, 129.41, 129.77, 139.76, 139.96 (12C, 2 $C_6H_5$), 153.05, 156.67 (2C, $C_6H_4$), 173.01 (CO); ESI-MS: m/z: calcd for $C_{33}H_{38}NaO_{13}$[M+Na]$^+$: 665.23, found: 665.23.

4-Methoxyphenyl (Sodium β-D-Glucopyranuronate)-(1→3)-β-D-Galactopyranoside (2)

Compound 6 (205 mg, 0.31 mmol) and $Pd(OH)_2$/C (42 mg, 20%) were suspended in MeOH/$H_2O$ (10:1, 5 mL) under argon. The mixture was stirred overnight under an atmosphere of hydrogen (1 atm), then the catalyst was filtered off through a pad of Celite. The Celite was washed with a MeOH/$H_2O$ gradient (6×10 mL, 10:0, 8:2, 6:4, 4:6, 2:8, 0:10). The filtrate was concentrated and passed over a Dowex® 50X8 (Na$^+$) ion-exchange column. After concentration the residue was purified by reversed-phase chromatography (RP-18, water) followed by P2 size-exclusion chromatography to give 2 (148 mg, 0.31 mmol, 96%) as a white solid.

$[\alpha]_D^{20}$ −40.7 (c 1.00, $H_2O$); $^1$H NMR (500 MHz, $D_2O$): δ 3.43 (t, J=8.3 Hz, 1H, H-2'), 3.48-3.56 (m, 2H, H-3', H-5'), 3.67-3.81 (m, 7H, H-5, H-6, H-4', OMe), 3.83 (dd, J=2.9, 9.8 Hz, 1 H, H-3), 3.90 (dd, J=8.0 Hz, 1 H, H-2), 4.22 (d, J=2.5 Hz, 1H, H-4), 4.68 (d, J=7.7 Hz, 1H, H-1'), 4.95 (d, J=7.9 Hz, 1H, H-1), 6.94, 7.09 (AA', BB' of AA'BB', J=9.0 Hz, 4H, $C_6H_4$); $^{13}$C NMR (126 MHz, $D_2O$): δ 55.71 (OMe), 60.70 (C-6), 67.94 (C-4), 69.63 (C-2), 71.73 (C-3'), 73.09 (C-2'), 75.05 (C-5'), 75.25 (C-5), 76.18 (C-4'), 82.37 (C-3), 101.29 (C-1), 103.61 (C-1'), 114.96, 118.10, 150.84, 154.61 (6C, $C_6H_4$), 175.92 (CO); HRMS: m/z: calcd for $C_{19}H_{26}NaO_{13}$ [M+H]$^+$: 485.1271, found: 485.1276.

4-Methoxyphenyl (Methyl 2,4-Di-O-Acetyl-β-D-Glucopyranuronate)-(1→3)-4-O-Acetyl-2,6-Di-O-Benzyl-β-D-Galactopyranoside (7)

A solution of 6 (470 mg, 0.73 mmol) in $Ac_2O$ (10 mL) was stirred at 80° C. for 90 min and then cooled to rt. Pyridine (6 mL) and DMAP (15 mg) were added and the reaction mixture was stirred for 3 days. The solvents were co-evaporated with toluene (5×5 mL). The residue dissolved in DCM (50 mL) and extracted with brine (50 mL) and water (50 mL). The organic phase was dried over $Na_2SO_4$ and filtered through cotton wool. After evaporation of the solvent the residue was dissolved in dry MeOH (14 mL) and anhydrous NaOAc (90 mg) was added. The mixture was stirred overnight, neutralized with Amberlyste® 15 (H$^+$) ion-exchange resin and filtered. The filtrate was concentrated and the residue purified by flash chromatography (petroleum ether/EtOAc, 2:1 to 1:1) to yield 7 (334 mg, 0.43 mmol, 57%) as a yellowish solid.

$[\alpha]_D^{20}$+34.3 (c 1.00, $CHCl_3$); $^1$H NMR (500 MHz, $CDCl_3$): δ 1.92, 2.01, 2.04 (3s, 9H, 3 OAc), 3.48 (dd, J=7.1, 10.1 Hz, 1H, H-6a), 3.55 (dd, J=4.8, 10.1 Hz, 1H, H-6b), 3.60 (m, 1 H, H-3'), 3.66, 3.69 (2s, 6H, 2 OMe), 3.77 (dd, J=5.4, 7.0 Hz, 1H, H-5), 3.80 (d, J=9.8 Hz, 1H, H-5'), 3.83 (dd, J=7.6, 9.7 Hz, 1H, H-2), 3.89 (dd, J=3.5, 9.7 Hz, 1H, H-3), 4.43 (A, B of AB, J=11.6 Hz, 2H, $CH_2Ph$), 4.64 (A of AB, J=11.5 Hz, 1H, $CH_2Ph$), 4.81 (d, J=7.6 Hz, 1H, H-1), 4.83-4.87 (m, H-1', H-2'), 4.97 (B of AB, J=11.5 Hz, 1H, $CH_2Ph$), 5.06 (t, J=9.5 Hz, 1H, H-4'), 5.36 (d, J=3.2 Hz, 1H, H-4), 6.72, 6.96 (AA', BB' of AA'BB', J=9.1 Hz, 4H, $C_6H_4$), 7.18-7.31 (m, 10H, 2 $C_6H_5$); $^{13}$C NMR (126 MHz, $CDCl_3$): δ 20.72, 20.76, 20.80 (3 $COCH_3$), 52.81, 55.63 (2 OMe), 68.95 (C-6), 69.33 (C-4), 71.87 (C-4'), 72.54 (C-5), 73.04 (C-5'), 73.26 (C-3'), 73.70 ($CH_2Ph$), 73.79 (C-2'), 75.31 ($CH_2Ph$), 77.24 (C-3), 79.26 (C-2), 100.15 (C-1'), 102.65 (C-1), 114.56, 118.24 (4C, $C_6H_4$), 127.76, 127.83, 127.98, 128.04, 128.41, 128.53, 137.87, 138.00 (12C, 2 $C_6H_5$), 151.35, 155.35 (2C, $C_6H_4$), 167.46, 170.15, 170.36, 170.38 (4 CO); ESI-MS: m/z: calcd for $C_{40}H_{46}NaO_{16}$ [M+Na]$^+$: 805.28, found: 805.34.

4-Methoxyphenyl (Methyl 2,4-Di-O-Acetyl-3-O-Sulfo-β-D-Glucopyranuronate)-(1→3)-4-O-Acetyl-2,6-Di-O-Benzyl-β-D-Galactopyranoside, Sodium Salt (8)

Compound 7 (334 mg, 0.43 mmol) was dissolved in DMF (5 mL) and $SO_3$·Py (370 mg, 2.34 mmol) was added. The mixture was stirred for 2 h at rt, then the reaction was quenched by stirring with $NaHCO_3$ (320 mg, 3.77 mmol) for 2 h. The solid was filtered off and the filter was washed with MeOH. The filtrate was passed over a Dowex® 50×8 (Na$^+$) ion-exchange column, concentrated and the residue was purified by flash chromatography (DCM/MeOH, 1:0 to 9:1) to give 8 (237 mg, 0.28 mmol, 65%) as a yellowish solid. During concentration after the flash chromatography a few drops of 0.1 M aq NaOH were added.

$[\alpha]_D^{20}$ −10.4 (c 1.01, MeOH); $^1$H NMR (500 MHz, $CD_3OD$): δ 1.89, 2.03, 2.06 (3s, 9H, 3 OAc), 3.48 (dd, J=7.4, 10.4 Hz, 1H, H-6a), 3.59 (dd, J=4.4, 10.5 Hz, 1H, H-6b), 3.69, 3.72 (2s, 6H, 2 OMe), 3.77 (dd, J=7.8, 9.6 Hz, 1H, H-2), 3.98 (dd, J=4.5, 7.4 Hz, 1H, H-5), 4.03 (m, 1H, H-3), 4.05 (d, J=10.2 Hz, 1H, H-5'), 4.46, 4.49 (A, B of AB, J=11.6 Hz, 2H, $CH_2Ph$), 4.60 (t, J=9.3 Hz, 1H, H-3'), 4.73, 4.92 (A, B of AB, J=11.8 Hz, 2H, $CH_2Ph$), 4.94 (d, J=7.5 Hz, 1H, H-2'), 4.96 (d, J=7.9 Hz, 1H, H-1'), 4.99 (d, J=8.0 Hz, 1 H, H-1), 5.06 (m, 1H, H-4'), 5.40 (d, J=3.6 Hz, 1H, H-4), 6.77, 7.00 (AA', BB' of AA'BB', J=9.1 Hz, 4H, $C_6H_4$), 7.23-7.35 (m, 8H, 2 $C_6H_5$), 7.39 (d, J=7.2 Hz, 2H, 2 $C_6H_5$); $^{13}$C NMR (126 MHz, $CD_3OD$): δ 19.32, 19.23, 19.64 (3 $COCH_3$), 51.68, 54.52 (2 OMe), 68.73 (C-6), 69.50 (C-4), 69.80 (C-4'), 71.36 (C-2'), 71.91 (C-5'), 72.52 (C-5), 72.83, 74.69 (2 $CH_2Ph$), 77.50 (C-3'), 78.57 (C-3), 78.59 (C-2), 100.04 (C-1), 102.01 (C-1'), 114.03, 117.64 (4C, $C_6H_4$), 127.14, 127.23, 127.36, 127.57, 127.81, 127.89, 138.02, 138.23 (12C, 2 $C_6H_5$), 151.29, 155.26 (2C, $C_6H_4$), 167.77, 170.07, 170.17, 170.64 (4 CO); ESI-MS: m/z: calcd for $C_{40}H_{46}O_{19}S$ [M]$^+$: 862.24, found: 862.42.

4-Methoxyphenyl (Disodium-3-O-Sulfo-β-D-Glucopyranuronate)-(1→3)-β-D-Galacto-Pyranoside (1)

Compound 8 (237 mg, 0.28 mmol) and $Pd(OH)_2$/C (48 mg, 20%) were suspended in MeOH/$H_2O$ (10:1, 5 mL) under argon. The reaction mixture was stirred for 9 h under an atmosphere of hydrogen (1 atm). The catalyst was filtered off through a pad of Celite and the pad was washed with a MeOH/$H_2O$ gradient (6×10 mL, 10:0, 8:2, 6:4, 4:6, 2:8, 0:10). The filtrate was concentrated and the residue was dissolved in MeOH/$H_2O$ (1:1, 8 mL). Then 1 M aq LiOH (6.5 mL) was added at −10° C. and the reaction mixture was allowed to warm to rt over 3 h, neutralized with Amberlyste® 15 (H$^+$) ion-exchange resin, filtered and concentrated. The residue was purified by reversed-phase chromatography (RP-18, water) and passed over a Dowex® 50X8 ($Na^+$) ion-exchange column. Final purification by P2 size-exclusion chromatography yielded 1 (142 mg, 0.24 mmol, 88%) as a solid.

[α]D[20] −19.2 (c 1.00, $H_2O$); $^1H$ NMR (500 MHz, $D_2O$): δ 3.63 (dd, J=8.0, 9.2 Hz, 1H, H-2'), 3.73 (m, 1H, H-4'), 3.75-3.81 (m, 6H, H-5, H-6, OMe), 3.85 (d, J=10.0 Hz, 1H, H-5'), 3.89 (dd, J=3.2, 9.9 Hz, 1H, H-3), 3.94 (dd, J=7.7, 9.8 Hz, 1H, H-2), 4.24 (d, J=3.1 Hz, 1H, H-4), 4.40 (t, J=9.2 Hz, 1H, H-3'), 4.81 (d, J=7.9 Hz, 1H, H-1'), 4.97 (d, J=7.7 Hz, 1H, H-1), 6.96, 7.11 (AA', BB' of AA'BB', J=9.2 Hz, 4H, $C_6H_4$); $^{13}C$ NMR (126 MHz, $D_2O$): δ 55.82 (OMe), 60.62 (C-6), 67.95 (C-4), 69.55 (C-2), 70.42 (C-4'), 71.86 (C-2'), 74.92 (C-5), 75.82 (C-5'), 82.49 (C-3), 83.30 (C-3'), 101.43 (C-1), 103.17 (C-1'), 115.02, 118.14, 150.89, 154.59 (6C, $C_6H_4$), 175.48 (CO); HRMS: m/z: calcd for $C_{19}H_{25}Na_2O_{16}S$[M +H]$^+$: 587.0659, found: 587.0665.

Scheme 2: Synthesis of the minimal HNK-1 polymer 25

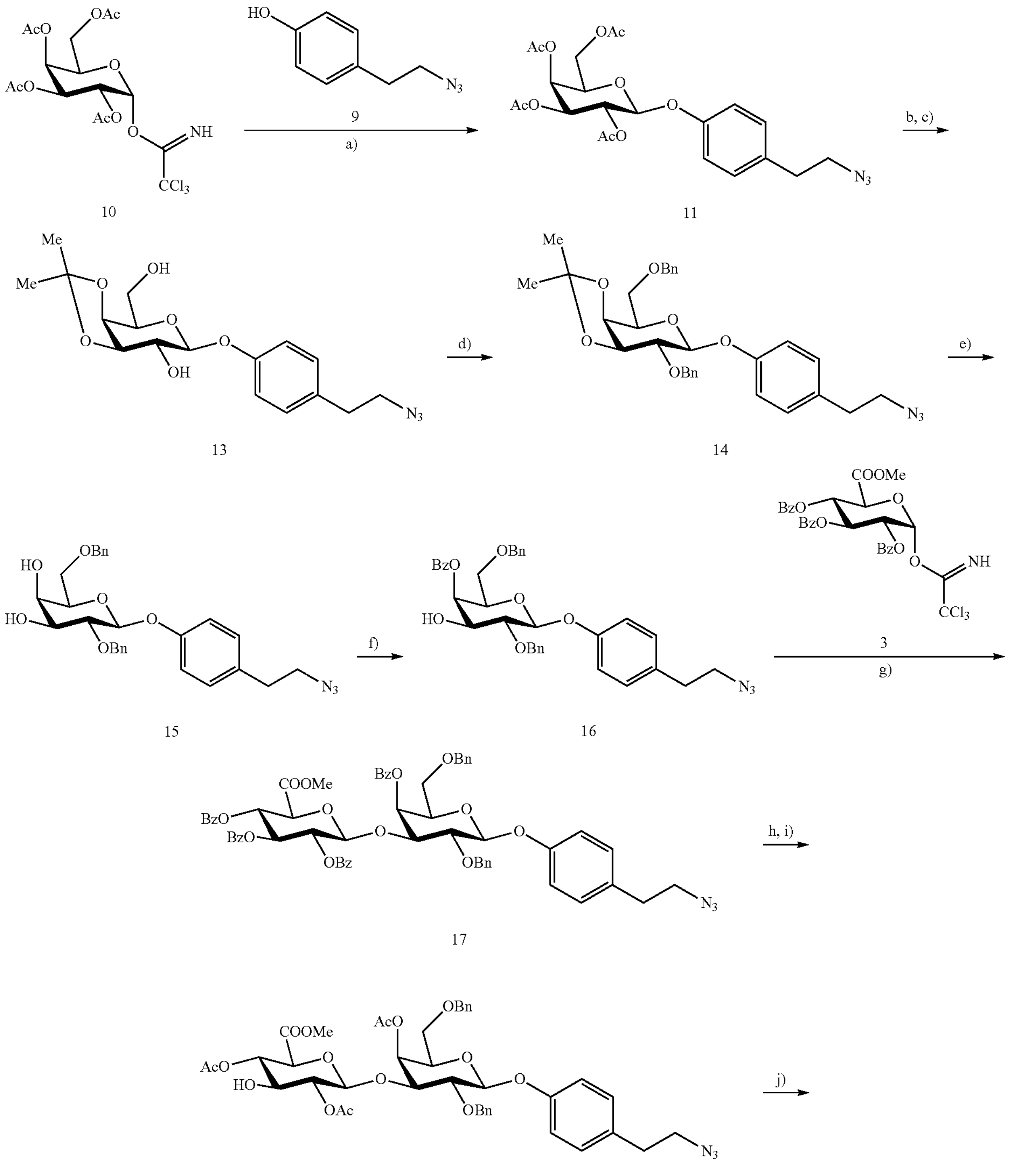

10 11 13 14 15 16 17 19

-continued
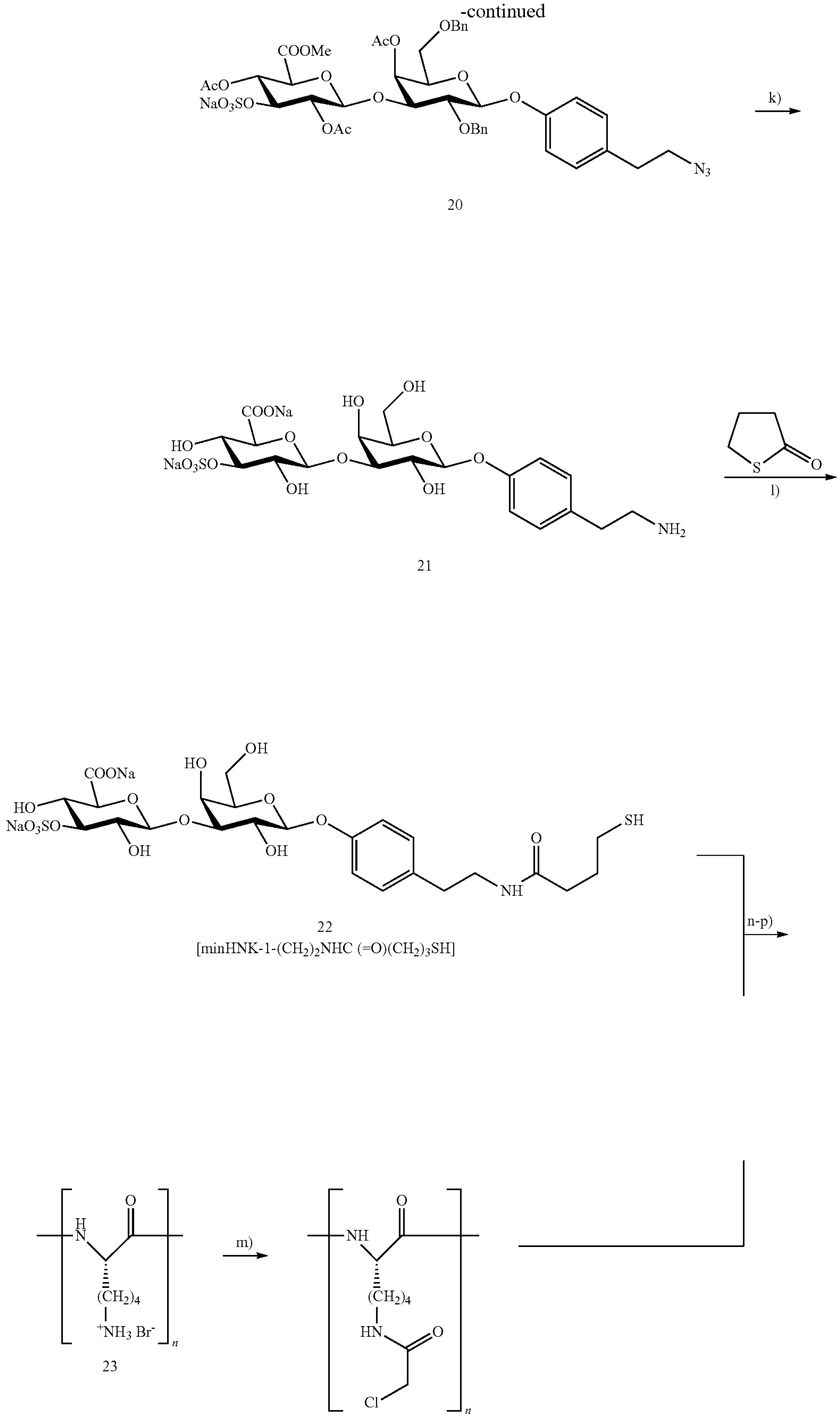
20
21
22
[minHNK-1-$(CH_2)_2NHC$ (=O)$(CH_2)_3SH$]
23
24

-continued

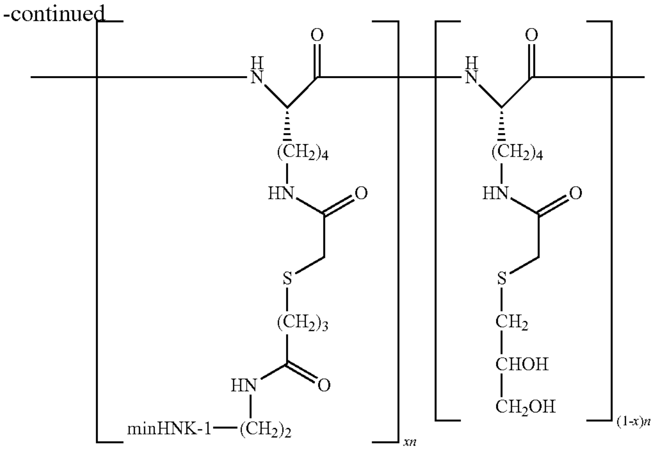

25

Reagents and conditions: a) TMSOTf, molecular sieves 4 Å, DCM, 0° C. to rt (53%); b) MeOH, NaOMe, rt, overnight (gives 12, 95%); c) 2,2-dimethoxypropane, p-TsOH (Ts: toluylsulfonyl), DMF, rt, overnight (75%); d) Crown ether15-crown-5, BnBr, 50% aq NaOH, DCM, overnight, 60° C., (83%); e) AcOH, $H_2O$, 60° C., overnight (quant.); f) trimethyl-orthobenzoate, p-TsOH, toluene, 45° C., overnight; AcOH, $H_2O$, 60° C., 2 h, (93%); g) TMSOTf, molecular sieves 4 Å, DCM, 0° C. to rt, 86%; h) LiOH in THF/$H_2O$ (89%); i) Ac2O, DMAP, pyr; MeOH, NaOAc MeOH (gives 18, 73%); j) $SO_3$•Py, DMF (91%); k) LiOH, THF/$H_2O$; $Pd(OH)_2$/C, $H_2$, MeOH/$H_2O$ (78%); l) dithiotreitol, thiobutyrolactone, TEA, DMF, 85° C. (59%); m) chloroacetic anhydride, 2,6-lutidine, DMF (96%); n) DMF, $H_2O$, DBU; thioglycerol, TEA: ultracentrifugation (70%).

4-(2-Azidoethyl)Phenol (9)

Tyramine (3.43 g, 25.0 mmol), $NaHCO_3$ (7.80 g, 92.8 mmol) and $CuSO_4·5H_2O$ (0.22 g, 0.9 mmol) were dissolved in water (30 mL). Triflic azide stock solution (40 mL), which was prepared according to Titz A. et al., Tetrahedron Letters 47:2383-2385 (2006), and MeOH (190 mL) were added to give a homogeneous mixture. The mixture was stirred at rt overnight, then diluted with water (150 mL) and extracted with EtOAc (3×150 mL). The organic layer was dried over $Na_2SO_4$ and the solvents were evaporated. The residue was purified by flash chromatography (petroleum ether/EtOAc, 1:0 to 4:1) to yield 9 (quant.) as colorless oil.

$^1$H NMR (500 MHz, $CDCl_3$): δ 2.81 (t, J=7.3 Hz, 2H, $CH_2CH_2N_3$), 3.44 (t, J=7.2 Hz, 2H, $CH_2CH_2N_3$), 6.77, 7.07 (AA', BB' of AA'BB', J=8.5 Hz, 4H, $C_6H_4$); $^{13}$C NMR (126 MHz, $CDCl_3$): δ 34.50 ($CH_2CH_2N_3$), 52.72 ($CH_2CH_2N_3$), 115.53, 129.96, 130.22, 154.39 (6C, $C_6H_4$); IR (film): 2105 $cm^{-1}$ ($N_3$).

4-(2-Azidoethyl)Phenyl 2,3,4,6-Tetra-O-Acetyl-β-D-Galactopyranoside (11)

To an ice-cooled suspension of 10 (8.30 g, 17.5 mmol) (Bukowski R et al., European Journal of Organic Chemistry 2001:2697-2705) and 4 A molecular sieves (3 g) in DCM (40 mL) was added 9 (4.00 g, 24.5 mmol) in DCM (40 mL) under argon. TfOH (0.45 mL, 2.5 mmol) was added dropwise and the reaction mixture was allowed to warm to rt overnight. After quenching with TEA (0.8 mL) the suspension was filtered and the filtrate was concentrated. The residue was purified by flash chromatography (petroleum ether/EtOAc, 9:1 to 3:2) to yield 11 (4.58 g, 9.28 mmol, 53%) as oil.

$[\alpha]_D^{20}$+6.1 (c 1.10, $CHCl_3$); $^1$H NMR (500 MHz, $CDCl_3$): δ 1.98, 2.02, 2.06, 2.15 (4s, 12H, 4 OAc), 2.82 (t, J=7.2 Hz, 2H, $CH_2CH_2N_3$), 3.45 (t, J=7.1 Hz, 2H, $CH_2CH_2N_3$), 4.02 (t, J=6.6 Hz, 1H, H-5), 4.13 (dd, J=6.3, 11.3 Hz, 1H, H-6a), 4.20 (dd, J=6.9, 11.2 Hz, 1H, H-6b), 4.99 (d, J=8.0 Hz, 1H, H-1), 5.08 (dd, J=3.4, 10.5 Hz, 1H, H-3), 5.40-5.48 (m, 2H, H-2, H-4), 6.93, 7.12 (AA', BB' of AA'BB', J=8.6 Hz, 4H, $C_6H_4$); $^{13}$C NMR (126 MHz, $CDCl_3$): δ 20.58, 20.65, 20.65, 20.73 (4 $COCH_3$), 34.52 ($CH_2CH_2N_3$), 52.51 ($CH_2CH_2N_3$), 61.36 (C-6), 66.89 (C-4), 68.67 (C-2), 70.85 (C-3), 71.01 (C-5), 99.78 (C-1), 117.19, 129.87, 133.01, 155.85 (6C, $C_6H_4$), 169.40, 170.13, 170.26, 170.36 (4 CO); ESI-MS: m/z: calcd for $C_{22}H_{27}N_3NaO_{10}$ $[M+Na]^+$: 516.17, found: 516.19; IR (film): 2101 $cm^{-1}$ ($N_3$).

4-(2-Azidoethyl)Phenyl β-D-Galactopyranoside (12)

A solution of 11 (4.58 g, 9.28 mmol) in MeOH (45 mL) was treated with 1 M NaOMe/MeOH (4.5 mL) under argon overnight. After neutralization with Amberlite® IR-120 ($H^+$) ion-exchange resin, the solvent was evaporated and the residue was purified by flash chromatography (DCM/MeOH, 1:0 to 4:1) to give 12 (2.86g, 8.79 mmol, 95%) as an oil.

$[\alpha]_D^{20}$ −38.1 (c 1.00, MeOH); $^1$H NMR (500 MHz, $CD_3OD$): δ 2.85 (t, J=7.1 Hz, 2H, $CH_2CH_2N_3$), 3.49 (t, J=7.1 Hz, 2H, $CH_2CH_2N_3$), 3.60 (dd, J=3.4, 9.7 Hz, 1H, H-3), 3.70 (m, 1H, H-5), 3.75-3.85 (m, 3H, H-2, H-6), 3.93 (d, J=3.2 Hz, 1H, H-4), 4.86 (d, J=7.8 Hz, 1H, H-1), 7.09, 7.20 (AA', BB' of AA'BB', J=8.6 Hz, 4H, $C_6H_4$); $^{13}$C NMR (126 MHz, $CD_3OD$): δ 35.49 ($CH_2CH_2N_3$), 53.75 ($CH_2CH_2N_3$), 62.44 (C-6), 70.25 (C-4), 72.34 (C-2), 74.89 (C-3), 76.96 (C-5), 103.11 (C-1), 118.00, 130.82, 133.65, 158.08 (6C, $C_6H_4$); ESI-MS: m/z: calcd for $C_{14}H_{19}N_3NaO_6$ $[M+Na]^+$: 348.13, found: 348.04; IR (film): 2112 $cm^{-1}$ ($N_3$).

4-(2-Azidoethyl)Phenyl 3,4-Isopropylidene-β-D-Galactopyranoside (13)

To a solution of 12 (2.86 g, 8.79 mmol) in DMF (30 mL) were added 2,2-dimethoxy-propane (2.50 mL, 19.3 mmol) and p-TsOH (37 mg) under argon. After stirring overnight at 80° C., the reaction mixture was neutralized with TEA (0.5 mL) and the solvents were evaporated. The residue was purified by flash chromatography (petroleum ether+0.5% TEA/EtOAc, 1:2 to 0:1) to yield 13 (2.39 g, 6.55 mmol, 75%) as an oil.

$[\alpha]_D^{20}$ −22.4 (c 1.10, $CHCl_3$); $^1$H NMR (500 MHz, $CDCl_3$): δ 1.34, 1.53 (2s, 6H, $Me_2C$), 2.42 (s, 2H, 2 OH), 2.81 (t, J=7.1 Hz, 2H, $CH_2CH_2N_3$), 3.44 (t, J=7.2 Hz, 2H, $CH_2CH_2N_3$), 3.78-3.85 (m, 2H, H-2, H-6a), 3.93-4.00 (m, 2H, H-6b, H-5), 4.14-4.21 (m, 2H, H-3, H-4), 4.78 (d, J=8.2 Hz, 1H, H-1), 6.95, 7.12 (AA', BB' of AA'BB', J=8.5 Hz, 4H, $C_6H_4$); $^{13}C$ NMR (126 MHz, $CDCl_3$): δ 26.33, 28.10 ($C(CH_3)_2$), 34.54 ($CH_2CH_2N_3$), 52.53 ($CH_2CH_2N_3$), 62.29 (C-6), 73.31 (C-2), 73.69 (C-5), 73.87 (C-4), 78.89 (C-3), 100.33 (C-1), 110.69 ($C(CH_3)_2$), 116.89, 129.95, 132.63, 155.78 (6C, $C_6H_4$); ESI-MS: m/z: calcd for $C_{17}H_{23}N_3NaO_6$ $[M+Na]^+$: 388.16, found: 388.06; IR (film): 2099 $cm^{-1}$ ($N_3$).

4-(2-Azidoethyl)Phenyl 2,6-Di-O-Benzyl-3,4-Isopropylidene-β-D-Galactopyranoside (14)

Compound 13 (1.02 g, 2.78 mmol) was dissolved in DCM (15 mL). 15-Crown-5 (55 μL, 0.28 mmol), 50% aq NaOH (37.5 mL) and benzylbromide (3.30 mL, 27.8 mmol) were added and the biphasic mixture was stirred overnight under reflux at 60° C. The reaction mixture was neutralized with 4 M aq HCl. The organic layer was separated and the aqueous phase extracted with DCM (2×50 mL) and. The combined organic layers were concentrated and the residue was purified by flash chromatography (petroleum ether+0.5% TEA/EtOAc, 1:0 to 3:1) to give 14 (1.26 g, 2.31 mmol, 83%) as a white solid.

$[\alpha]_D^{20}$ +8.4 (c 1.00, $CHCl_3$); $^1H$ NMR (500 MHz, $CDCl_3$): δ 1.28, 1.34 (2s, 6H, $Me_2C$), 2.76 (t, J=7.3 Hz, 2H, $CH_2CH_2N_3$), 3.37 (t, J=7.3 Hz, 2H, $CH_2CH_2N_3$), 3.60 (dd, J=6.8, 7.9 Hz, 1H, H-2), 3.69-3.80 (m, 2H, H-6), 3.97 (ddd, J=1.8, 4.7, 6.8 Hz, 1H, H-5), 4.13 (dd, J=2.0, 5.7 Hz, 1H, H-4), 4.18 (m, 1H, H-3), 4.46, 4.54 (A, B of AB, J=11.8 Hz, 2H, $CH_2Ph$), 4.78-4.85 (m, 3H, $CH_2Ph$, H-1), 6.69, 7.03 (AA', BB' of AA'BB', J=8.6 Hz, 4H, $C_6H_4$), 7.15-7.28 (m, 8H, 2 $C_6H_5$), 7.34 (d, J=7.4 Hz, 2H, 2 $C_6H_5$); $^{13}C$ NMR (126 MHz, $CDCl_3$): δ 26.41, 27.81 ($C(CH_3)_2$), 34.62 ($CH_2CH_2N_3$), 52.62 ($CH_2CH_2N_3$), 69.60 (C-6), 72.72 (C-5), 73.67 (C-4), 73.69 (2C, 2 $CH_2Ph$), 79.08 (C-3), 79.26 (C-2), 101.09 (C-1), 110.27 ($C(CH_3)_2$), 117.23 (2C, $C_6H_4$), 127.63, 127.69, 127.72, 128.26, 128.32, 128.40 (8C, 2 $C_6H_5$), 129.80 (2C, $C_6H_4$), 132.19, 138.14 (2 $C_6H_5$), 138.29, 156.26 ($C_6H_4$); ESI-MS: m/z: calcd for $C_{31}H_{35}N_3NaO_6[M+Na]^+$: 568.25, found: 568.21; IR (KBr): 2096 $cm^{-1}$ ($N_3$).δ

4-(2-Azidoethyl)Phenyl 2,6-Di-O-Benzyl-β-D-Galactopyranoside (15)

A solution of 14 (1.26 g, 2.31 mmol) in 90% aq AcOH (50 mL) was stirred at 60° C. stirred overnight. The solvents were evaporated and the residue was purified by flash chromatography (DCM/MeOH, 1:0 to 9:1) to give 15 (1.17 g, 2.31 mmol, quant) as an oil.

$[\alpha]_D^{20}$ −9.9 (c 1.10, $CHCl_3$); $^1H$ NMR (500 MHz, $CDCl_3$): δ 2.76 (t, J=7.3 Hz, 2H, $CH_2CH_2N_3$), 3.38 (t, J=7.3 Hz, 2H, $CH_2CH_2N_3$), 3.59 (dd, J=3.3, 9.5 Hz, 1H, H-3), 3.62-3.76 (m, 4H, H-2, H-5, H6), 3.92 (d, J=3.2 Hz, 1H, H-4), 4.48 (s, 2H, $CH_2Ph$), 4.69 (A of AB, J=11.5 Hz, 1H, $CH_2Ph$), 4.87 (d, J=7.7 Hz, 1H, H-1), 4.96 (B of AB, J=11.5 Hz, 1H, $CH_2Ph$), 6.97, 7.05 (AA', BB' of AA'BB', J=8.5 Hz, 4H, $C_6H_4$), 7.15-7.31 (m, 10H, 2 $C_6H_5$); $^{13}C$ NMR (126 MHz, $CDCl_3$): δ 34.58 ($CH_2CH_2N_3$), 52.59 ($CH_2CH_2N_3$), 68.92 (C-4), 69.41 (C-6), 73.20 (C-3), 73.74 (C-5), 73.81, 74.91 (2 $CH_2Ph$), 78.87 (C-2), 101.86 (C-1), 117.19 (2C, $C_6H_4$), 127.75, 127.83, 128.03, 128.27, 128.47, 128.60 (8C, 2 $C_6H_5$), 129.83 (2C, $C_6H_4$), 132.33, 137.87 (2 $C_6H_5$), 138.14, 156.13 ($C_6H_4$); ESI-MS: m/z: calcd for $C28H_{31}N_3NaO_6[M+Na]^+$: 528.22, found: 528.22; IR (film): 2098 $cm^{-1}$ ($N_3$).

4-(2-Azidoethyl)Phenyl 4-O-benzoyl-2,6-di-O-benzyl-β-D-Galactopyranoside (16)

To a solution of 15 (1.17 g, 2.31 mmol) in toluene (15 mL) were added trimethylortho-benzoate (0.64 mL, 3.72 mmol) and p-TsOH (118 mg, 0.62 mmol). The mixture was stirred at 45° C. overnight, then concentrated and the residue dissolved in 90% aq AcOH (15 mL). The solution was stirred for 2 h at 60° C., concentrated, and the residue was purified by flash chromatography (petroleum ether/EtOAc, 9:1 to 7:3) to yield 16 (1.30 g, 2.14 mmol, 93%) as a colorless oil.

$[\alpha]_D^{20}$ −8.4 (c 1.00, $CHCl_3$); $^1H$ NMR (500 MHz, $CDCl_3$): δ 2.83 (t, J=7.3 Hz, 2H, $CH_2CH_2N_3$), 3.44 (t, J=7.3 Hz, 2H, $CH_2CH_2N_3$) 3.60-3.66 (m, 2H, H-6), 3.87 (dd, J=7.4, 9.6 Hz, 1H, H-2), 3.92 (dd, J=3.5, 9.6 Hz, 1H, H-3), 3.96 (t, J=6.2 Hz, 1H, H-5), 4.41, 4.48 (A, B of AB, J=11.7 Hz, 2H, $CH_2Ph$), 4.78 (A of AB, J=11.2 Hz, 1 H, $CH_2Ph$), 4.99-5.07 (m, 2H, H-1, $CH_2Ph$), 5.63 (d, J=2.8 Hz, 1H, H-4), 7.06, 7.12 (AA', BB' of AA'BB', J=8.5 Hz, 4H, $C_6H_4$), 7.18-7.35 (m, 10H, 2 $C_6H_5$), 7.43 (t, J=7.8 Hz, 2H, $C_6H_5$), 7.56 (t, J=7.4 Hz, 1 H, $C_6H_5$), 8.04-8.09 (m, 2H, $C_6H_5$); $^{13}C$ NMR (126 MHz, $CDCl_3$): δ 34.62 ($CH_2CH_2N_3$), 52.63 ($CH_2CH_2N_3$), 68.61 (C-6), 70.25 (C-4), 72.21 (C-3), 73.28 (C-5), 73.71, 75.13 (2 $CH_2Ph$), 79.15 (C-2), 101.89 (C-1), 117.07 (2C, $C_6H_4$), 127.76, 127.78, 128.04, 128.29, 128.39, 128.49, 128.58, 129.57 (12C, 3 $C_6H_5$), 129.93 (2C, $C_6H_4$), 130.10, 132.46, 133.38, 137.79 (6C, 3 $C_6H_5$), 138.06, 156.17 ($C_6H_4$), 166.38 (CO); ESI-MS: m/z: calcd for $C_{35}H_{35}N_3NaO_7$ $[M+Na]^+$: 532.24, found: 532.28; IR (film): 2102 $cm^{-1}$ ($N_3$).

4-(2-Azidoethyl)Phenyl (Methyl 2,3,4-Tri-O-Benzoyl-β-D-Glucopyranuronate)-(1→3)-4-O-Benzoyl-2,6-Di-O-Benzyl-β-D-Galactopyranoside (17)

Under argon tricholoroacetimidate 3 (1.75 g, 2.63 mmol), 16 (1.30 g, 2.14 mmol) and activated 4 A molecular sieves (2 g) were suspended in DCM (25 mL). The mixture was stirred for 1 h at rt and then cooled to 0° C. TMSOTf (58.4 μL, 0.32 mmol) was added dropwise. The reaction mixture was allowed to warm to rt overnight, and was then neutralized with TEA (150 μL) and concentrated. The residue was purified by chromatography (petroleum ether/EtOAc, 9:1 to 7:3) to yield 17 (2.04 g, 1.84 mmol, 86%) as a white solid.

$[\alpha]_D^{20}$ +25.2 (c 1.10, $CHCl_3$); $^1H$ NMR (500 MHz, $CDCl_3$): δ 2.84 (t, J=7.3 Hz, 2H, $CH_2CH_2N_3$), 3.46 (t, J=7.2 Hz, 2H, $CH_2CH_2N_3$), 3.61 (dd, J=7.3, 10.1 Hz, 1H, H-6a), 3.67 (s, 3H, OMe), 3.72 (dd, J=4.7, 10.2 Hz, 1 H, H-6b), 3.98 (dd, J=7.9, 9.5 Hz, 1 H, H-2), 4.02 (dd, J=5.3, 6.5 Hz, 1H, H-5), 4.15 (d, J=9.8 Hz, 1H, H-5'), 4.24 (dd, J=3.4, 9.5 Hz, 1H, H-3), 4.48 (A, B of AB, J=11.5 Hz, 2H, $CH_2Ph$), 4.55, 4.91 (A, B of AB, J=10.7 Hz, 2H, $CH_2Ph$), 5.02 (d, J=7.7 Hz, 1H, H-1), 5.39 (d, J=7.4 Hz, 1H, H-1'), 5.47 (dd, J=7.4, 9.1 Hz, 1H, H-2'), 5.69 (t, J=9.5 Hz, 1H, H-4'), 5.77 (t, J=9.3 Hz, 1H, H-3'), 5.81 (d, J=3.3 Hz, 1H, H-4), 7.02, 7.10 (AA', BB' of AA'BB', J=8.7 Hz, 4H, $C_6H_4$), 7.22-7.46, 7.48-7.53, 7.56-7.66, 7.76-7.81, 7.88-7.93, 8.05-8.10 (m, 30H, 6 $C_6H_5$); $^{13}C$ NMR (126 MHz, $CDCl_3$): δ 34.60 ($CH_2CH_2N_3$), 52.59 ($CH_2CH_2N_3$), 52.86 (OMe), 69.06 (C-6), 70.01 (C-4), 70.06 (C-4'), 71.83 (C-2'), 72.24 (C-3'), 72.94 (C-5'), 73.67 (C-5), 73.73, 75.25 (2 $CH_2Ph$), 76.26 (C-3), 79.77 (C-2), 100.3 (C-1'), 101.81 (C-1), 117.02 (2C, $C_6H_4$), 127.69, 127.76, 127.98, 128.10, 128.30, 128.37, 128.43, 128.56, 128.75, 128.94, 129.09, 129.60, 129.77, 129.82, 129.87, 129.94, 130.10, 132.39, 132.92, 133.08, 133.26, 133.38, 137.85, 137.92, 156.09 (40C, 6 $C_6H_5$, $C_6H_4$), 164.47, 165.00, 165.51, 165.64, 167.16 (5 CO); ESI-MS: m/z: calcd for $C_{63}H_{57}N_3NaO_{16}$ $[M+Na]^+$: 1134.36, found: 1134.47; IR (KBr): 2099 $cm^{-1}$ ($N_3$).

4-(2-Azidoethyl)Phenyl (β-D-Glucopyranuronate)-(1→3)-2,6-Di-O-Benzyl-P-D-Galacto-Pyranoside (18)

Compound 17 (2.04 g, 1.84 mmol) was suspended in THF (14 mL) and the suspension was cooled to −10° C. Then 2 M aq LiOH (10 mL) was added dropwise. The reaction mixture was stirred overnight and allowed to warm to rt. After neutralization with Amberlite® IR-120 ($H^+$) ion-exchange resin and filtration, the solvents were evaporated, the residue was dissolved in THF/$H_2O$ (2:3, 16 mL) and treated with TFA (8 mL) for 30 min. The mixture was evaporated to dryness and the residue was purified by reversed-phase chromatography (RP-18, MeOH/water, 0:1 to 3:1) to give 18 (1.12 g, 1.64 mmol, 89%) as a solid.

$[\alpha]_D^{20}$ −48.1 (c 1.00, MePH); $^1$H NMR (500 MHz, $CD_3OD$): δ 2.79 (t, J=7.0 Hz, 2H, $CH_2CH_2N_3$), 3.35-3.47 (m, 4H, H-2', H-3', $CH_2CH_2N_3$), 3.53 (t, J=9.1 Hz, 1H, H-4'), 3.73 (m, 2H, H-6), 3.77 (d, J=9.8 Hz, 1H, H-5'), 3.81-3.89 (m, 2H, H-3, H-5), 3.94 (m, 1H, H-2), 4.06 (d, J=2.5 Hz, 1 H, H-4), 4.53 (s, 2H, $CH_2Ph$), 4.74 (d, J=7.3 Hz, 1 H, H-1'), 4.88-4.95 (m, 2H, $CH_2Ph$), 4.99 (d, J=7.7 Hz, 1 H, H-1), 7.02, 7.12 (AA', BB' of AA'BB', J=8.5 Hz, 4H, $C_6H_4$), 7.20-7.34 (m, 8H, 2 $C_6H_5$), 7.41 (d, J=7.1 Hz, 2H, 2 $C_6H_5$); $^{13}$C NMR (126 MHz, $CD_3OD$): δ 33.97 ($CH_2CH_2N_3$), 52.19 ($CH_2CH_2N_3$), 68.85 (C-4), 69.18 (C-6), 71.78 (C-4'), 72.86 ($CH_2Ph$), 73.32 (C-2'), 73.58 (C-5), 74.69 ($CH_2Ph$), 74.93 (C-5'), 75.83 (C-3'), 78.50 (C-2), 80.64 (C-3), 101.39 (C-1), 104.07 (C-1'), 116.43 (2C, $C_6H_4$), 127.12, 127.21, 127.25, 127.75, 127.87, 128.23 (10C, 2 $C_6H_5$), 129.44, 132.31 (3C, $C_6H_4$), 138.22, 138.38 (2 $C_6H_5$), 156.25 ($C_6H_4$), 171.27 (CO); ESI-MS: m/z: calcd for $C_{34}H_{39}N_3NaO_{12}$ [M+Na]$^+$: 704.24, found: 704.30; IR (KBr): 2099 cm$^{-1}$ ($N_3$).

4-(2-Azidoethyl)Phenyl (Methyl 2,4-Di-O-Acetyl-β-D-Glucopyranuronate)-(1→3)-4-O-Acetyl-2,6-Di-O-Benzyl-β-D-Galactopyranoside (19)

A solution of 18 (900 mg, 1.32 mmol) in $Ac_2O$ (15 mL) was stirred at 80° C. for 1 h and then cooled to rt. Pyridine (9 mL) and DMAP (25 mg) were added and the reaction mixture was stirred for 3 days. The solvents were co-evaporated with toluene (5×5 mL). The residue was dissolved in DCM (50 mL) and extracted with brine (50 mL) and water (50 mL). The organic phase was dried over $Na_2SO_4$ and filtered through cotton wool. After evaporation of the solvent the residue was dissolved in dry MeOH (20 mL) and anhydrous NaOAc (100 mg) was added. The mixture was stirred overnight, neutralized with Amberlyste® 15 ($H^+$) ion-exchange resin and filtered. The filtrate was concentrated and the residue purified by flash chromatography (petroleum ether/EtOAc, 2:1 to 2:3) to yield 19 (794 mg, 0.97 mmol, 73%) as a yellowish solid.

$[\alpha]_D^{20}$ −32.6 (c 1.00, $CHCl_3$); $^1$H NMR (500 MHz, $CDCl_3$): δ 1.92, 2.01, 2.04 (3s, 9H, 3 OAc), 2.77 (t, J=7.2 Hz, 2H, $CH_2CH_2N_3$), 3.40 (t, J=7.2 Hz, 2H, $CH_2CH_2N_3$), 3.48 (dd, J=7.1, 10.1 Hz, 1H, H-6a), 3.55 (dd, J=4.8, 10.2 Hz, 1H, H-6b), 3.61 (m, 1H, H-3'), 3.67 (s, 3H, OMe), 3.78-3.83 (m, 2H, H-5, H-5'), 3.86 (dd, J=7.6, 9.7 Hz, 1H, H-2), 3.91 (dd, J=3.3, 9.6 Hz, 1H, H-3), 4.43 (A, B of AB, J=11.7 Hz, 2H, $CH_2Ph$), 4.64 (A of AB, J=11.6 Hz, 1H, $CH_2Ph$), 4.81-4.88 (m, 2H, H-1, H-2), 4.91 (d, J=7.6 Hz, 1H, H-1'), 4.95 (B of AB, J=10.6 Hz, 1H, $CH_2Ph$), 5.07 (t, J=9.5 Hz, 1H, H-4'), 5.38 (d, J=3.0 Hz, 1H, H-4), 6.96, 7.04 (AA', BB' of AA'BB', J=8.5 Hz, 4H, $C_6H_4$), 7.18-7.31 (m, 10H, 2 $C_6H_5$); $^{13}$C NMR (126 MHz, $CDCl_3$): δ 20.69, 20.72, 20.76 (3 $COCH_3$), 34.59 ($CH_2CH_2N_3$), 52.58 ($CH_2CH_2N_3$), 52.79 ($OCH_3$), 68.93 (C-6), 69.30 (C-4), 71.91 (C-4'), 72.53 (C-5), 73.10 (C-5'), 73.38 (C-3'), 73.70 ($CH_2Ph$), 73.87 (C-2'), 75.31 ($CH_2Ph$), 77.24 (C-3), 79.19 (C-2), 100.10 (C-1'), 101.71 (C-1), 117.04 (2C, $C_6H_4$), 127.76, 127.80, 127.96, 128.01, 128.40, 128.49 (10C, 2 $C_6H_5$), 129.85, 132.41 (3C, $C_6H_4$), 137.87, 137.96 (2 $C_6H_5$), 156.08 ($C_6H_4$), 167.42, 170.11, 170.29, 170.32 (4 CO); ESI-MS: m/z: calcd for $C_{41}H_{47}N_3NaO_{15}$ [M+Na]$^+$: 844.29, found: 844.39; IR (KBr): 2101 cm$^{-1}$ ($N_3$).

4-(2-Azidoethyl)Phenyl (Methyl 2,4-Di-O-Acetyl-3-O-Sulfo-β-D-Glucopyranuronate)-(1→3)-4-O-Acetyl-2,6-Di-O-Benzyl-β-D-Galactopyranoside, Sodium Salt (20)

Compound 19 (794 mg, 0.97 mmol) was dissolved in dry DMF (10 mL) and $SO_3$·Py (846 mg, 5.31 mmol) was added. The mixture was stirred for 2 h at rt and quenched by stirring with $NaHCO_3$ (719 mg, 8.56 mmol) for 2 h. The solid was filtered off and the filter was washed with MeOH. The filtrate was passed over a Dowex 50X8 ($Na^+$) ion-exchange column. The filtrate was concentrated and the residue was purified by flash chromatography (DCM/MeOH, 1:0 to 9:1) to give 20 (808 mg, 0.88 mmol, 91%) as a yellowish solid. During concentration after the flash chromatography a few drops of 0.1 M aq NaOH were added.

$[\alpha]_D^{20}$ −18.3 (c 1.00, MeOH); $^1$H NMR (500 MHz, $CD_3OD$): δ 1.97, 2.09, 2.11 (3s, 9H, 3 OAc), 2.86 (t, J=7.0 Hz, 2H, $CH_2CH_2N_3$), 3.50 (t, J=7.0 Hz, 2H, $CH_2CH_2N_3$), 3.54 (dd, J=7.4, 10.4 Hz, 1H, H-6a), 3.65 (dd, J=4.4, 10.4 Hz, 1H, H-6b), 3.75 (s, 3H, OMe), 3.86 (dd, J=7.9, 9.5 Hz, 1H, H-2), 4.07 (dd, J=4.6, 7.1 Hz, 1H, H-5), 4.09-4.14 (m, 2H, H-3, H-5'), 4.49-4.57 (m, 2H, $CH_2Ph$), 4.66 (t, J=9.2 Hz, 1H, H-3'), 4.80 (A of AB, J=10.7 Hz, 1H, $CH_2Ph$), 4.96-5.03 (m, 2H, $CH_2Ph$, H-2'), 5.06 (d, J=7.9 Hz, 1H, H-1'), 5.11-5.17 (m, 2H, J=8.2 Hz, H-1, H-4') 5.48 (d, J=3.6 Hz, 1H, H-4), 7.07, 7.18 (AA', BB' of AA'BB', J=8.5 Hz, 4H, $C_6H_4$), 7.29-7.44 (m, 10H, 2 $C_6H_5$); $^{13}$C NMR (126 MHz, $CD_3OD$): δ 20.87, 21.20 (3C, 3 $COCH_3$), 35.50 ($CH_2CH_2N_3$), 53.24 ($CH_2CH_2N_3$), 53.71 (OMe), 70.27 (C-6), 71.08 (C-4), 71.37 (C-4'), 72.95 (C-2'), 73.50 (C-5'), 74.14 (C-5), 74.41, 76.26 (2 $CH_2Ph$), 78.98 (C-3'), 80.02 (C-3), 80.11 (C-2), 101.62 (C-1'), 102.61 (C-1), 117.93 (2C, $C_6H_4$), 128.69, 128.79, 128.90, 129.17, 129.37, 129.43 (10C, 2 $C_6H_5$), 131.02, 134.06 (3C, $C_6H_4$), 139.56, 139.72 (2 $C_6H_5$), 157.58 ($C_6H_4$), 164.89, 169.39, 171.64, 171.75 (4 CO); ESI-MS: m/z: calcd for $C_{41}H_{46}N_3O_{18}S$ [M−H]$^-$: 900.25, found: 900.42; IR (KBr): 2101 cm$^{-1}$ ($N_3$).

4-(2-Aminoethyl)Phenyl (Disodium 3-O-sulfo-β-D-Glucopyranuronate)-(1→3)-β-D-Galacto-Pyranoside (21)

To a solution of 20 (470 mg, 0.51 mmol) in THF/$H_2O$ (10:1, 10 mL) was added 2 M aq LiOH (2 mL) at −10° C. The reaction mixture was allowed to warm to rt and was stirred overnight. The mixture was neutralized with Amberlyste 15 ($H^+$) ion-exchange resin and filtered. The filtrate was passed over a Dowex® 50X8 ($Na^+$) ion-exchange column with MeOH and concentrated. The residue was purified by flash chromatography (DCM/MeOH/$H_2O$, 10:3:0.3). A few drops of 0.1 M aq NaOH were added during concentration of the product, which was then dissolved in MeOH (4.5 mL) and $H_2O$ (3.75 mL). AcOH (0.2 mL) and $Pd(OH)_2$/C (94 mg, 20%) were added under argon and the reaction mixture was stirred overnight under an atmosphere of hydrogen (1 atm). The catalyst was filtered off through a pad of Celite and the pad was washed with MeOH and a few drops of $H_2O$. The filtrate was concentrated and the residue purified by P2 size-exclusion chromatography to yield 21 (238 mg, 0.40 mmol, 78%) as a colorless solid after lyophilization.

$[\alpha]_D^{20}$ −25.6 (c 1.00, $H_2O$); $^1$H NMR (500 MHz, $D_2O$): 52.99 (t, J=7.0 Hz, 2H, $CH_2CH_2NH_2$), 3.28 (t, J=7.1 Hz, 2H, $CH_2CH_2NH_2$), 3.66 (t, J=8.4 Hz, 1H, H-2'), 3.71-3.88 (m, 5H, H5, H-6, H-4', H-5'), 3.92 (dd, J=3.2, 9.9 Hz, 1H, H-3), 3.99 (t, J=8.6 Hz, 1 H, H-2), 4.26 (d, J=3.1 Hz, 1H, H-4), 4.39 (t, J=9.0 Hz, 1H, H-3'), 4.82 (d, J=7.9 Hz, 1H, H-1'), 5.12 (d, J=7.7 Hz, 1H, H-1), 7.17, 7.32 (AA', BB' of AA'BB', J=8.0 Hz, 4H, $C_6H_4$); $^{13}$C NMR (126 MHz, $D_2O$): δ 31.97 ($CH_2CH_2NH_2$), 40.65 ($CH_2CH_2NH_2$), 60.78 (C-6), 68.05 (C-4), 69.02 (C-2), 70.50 (C-4'), 72.03 (C-2'), 75.10 (2C, C-5, C-5'), 82.43 (C-3), 83.60 (C-3'), 100.46 (C-1), 103.24 (C-1'), 117.01, 130.30, 131.29, 155.75 (6C, $C_6H_4$), 175.45 (CO); ESI-MS: m/z: calcd for $C_{20}H_{27}NNa_2O_{15}S$ [M−2Na+H]$^-$: 554.12, found: 554.07.

4-(2-(4-Mercaptobutanamido)Ethyl)Phenyl (Disodium-3-O-Sulfo-β-D-Glucopyranuronate)-(1→3)-β-D-Galactopyranoside (22)

To a suspension of 21 (238 mg, 0.40 mmol) in DMF (8 mL) were added dithiothreitol (112 mg, 0.72 mmol), thiobutyrolactone (343 μL, 4 mmol), and TEA (552 μL, 4 mmol). The mixture was stirred for 18 h at 85° C. The solvent was co-evaporated with toluene (3×5 mL) and the residue purified by flash chromatography (DCM/MeOH/$H_2O$, 10:5:1). A few drops of 0.1 M aq NaOH were added during concentration of the product. Lyophilization gave 22 (164 mg, 0.234 mmol, 59%) as a colorless solid.

$[\alpha]_D^{20}$ −20.2 (c 1.00, $H_2O$); $^1H$ NMR (500 MHz, $D_2O$): δ 1.72-1.85 (m, 2H, $CH_2CH_2CH_2SH$), 2.28 (t, J=7.2 Hz, 2H, $CH_2CH_2CH_2SH$), 2.37 (t, J=7.2 Hz, 2H, $CH_2CH_2CH_2SH$), 2.83 (t, J=6.5 Hz, 2H, $CH_2CH_2NH$), 3.49 (t, J=6.5 Hz, 2H, $CH_2CH_2NH$), 3.67 (dd, J=8.1, 9.1 Hz, 1H, H-2'), 3.73-3.91 (m, 5H, H-5, H6, H-4', H-5'), 3.94-4.02 (m, 2H, H-2, H-3), 4.29 (d, J=2.7 Hz, 1H, H-4), 4.39 (t, J=9.1 Hz, 1H, H-3'), 4.84 (d, J=7.9 Hz, 1H, H-1'), 5.13 (d, J=7.4 Hz, 1H, H-1), 7.14, 7.27 (AA', BB' of AA'BB', J=8.5 Hz, 4H, $C_6H_4$); $^{13}C$ NMR (126 MHz, $D_2O$): δ 22.87 ($CH_2CH_2CH_2SH$), 29.44 ($CH_2CH_2CH_2SH$), 33.63 ($CH_2CH_2NH$), 34.34 ($CH_2CH_2CH_2SH$), 40.25 ($CH_2CH_2NH$), 60.77 (C-6), 68.04 (C-4), 69.03 (C-2), 70.47 (C-4'), 72.02 (C-2'), 75.10 (C-5), 76.10 (C-5'), 82.48 (C-3), 83.62 (C-3'), 100.67 (C-1), 103.26 (C-1'), 116.72, 130.19, 133.93, 155.24 (6C, $C_6H_4$), 175.43, 175.79 (2 CO); HRMS: m/z: calcd for $C_{24}H_{33}NNa_2O_{16}S_2$ $[M+H]^+$: 702.1109, found: 702.1104.

Chloroacetylated Polylysine (24)

Polylysine hydrobromide (23) (Sigma P2636, MW 30-70 kD, 0.50 g, 2.4 mmol) was suspended in a mixture of DMF (5 mL) and 2,6-lutidine (1.25 mL) under argon. The suspension was cooled to 0° C. and a solution of chloroacetic anhydride (513 mg, 3.00 mmol) in DMF (1 mL) was added slowly. The resulting clear solution was stirred for 16 h at 0° C. The product was precipitated by dropwise addition of the reaction mixture to a stirred solution of ethanol/ether (1:1, 40 mL). The precipitate was filtered off, washed with ethanol/ether (1:1, 20 mL) and concentrated to give 24 (449 mg, 96%). The $^1H$ NMR data were in accordance with literature values (G. Thoma et al., J Am Chem Soc 1999, 121:5919-5929).

Minimal HNK-1 Polymer (25)

To a solution of 24 (80.2 mg, 0.39 mmol) in DMF (4 mL) were subsequently added 22 (110 mg, 0.16 mmol), water (200 μL) and DBU (88 μL, 0.59 mmol) in DMF (0.8 mL). After stirring for 1 h thioglycerol (102 μL, 1.18 mmol) and TEA (164 μL, 1.18 mmol) were added and the reaction mixture was stirred for 18 h. The product was precipitated by dropwise addition of the reaction mixture to a stirred solution of ethanol/ether (1:1, 30 mL). The precipitate was filtered off, washed with ethanol/ether (1:1, 15 mL) and dried. Further purification was achieved by means of ultrafiltration. The dried product was dissolved in water (10 mL) and ultracentrifugation was performed using two Sartorius Stedim Vivaspin 6 tubes (volume, 6 mL, diameter, 17 mm, molecular weight cutoff 5000). The ultrafiltration was repeated four times from 10 mL down to 3 mL, on each occasion the volume was filled up with water. Lyophilization gave the HNK-1 polymer 25 (139 mg, 70%) According to $^1H$ NMR, the product contained approximately 44% monomer carbohydrate units linked to the polymer.

Scheme 3: Synthesis of the minimal HNK-1 polymer 30

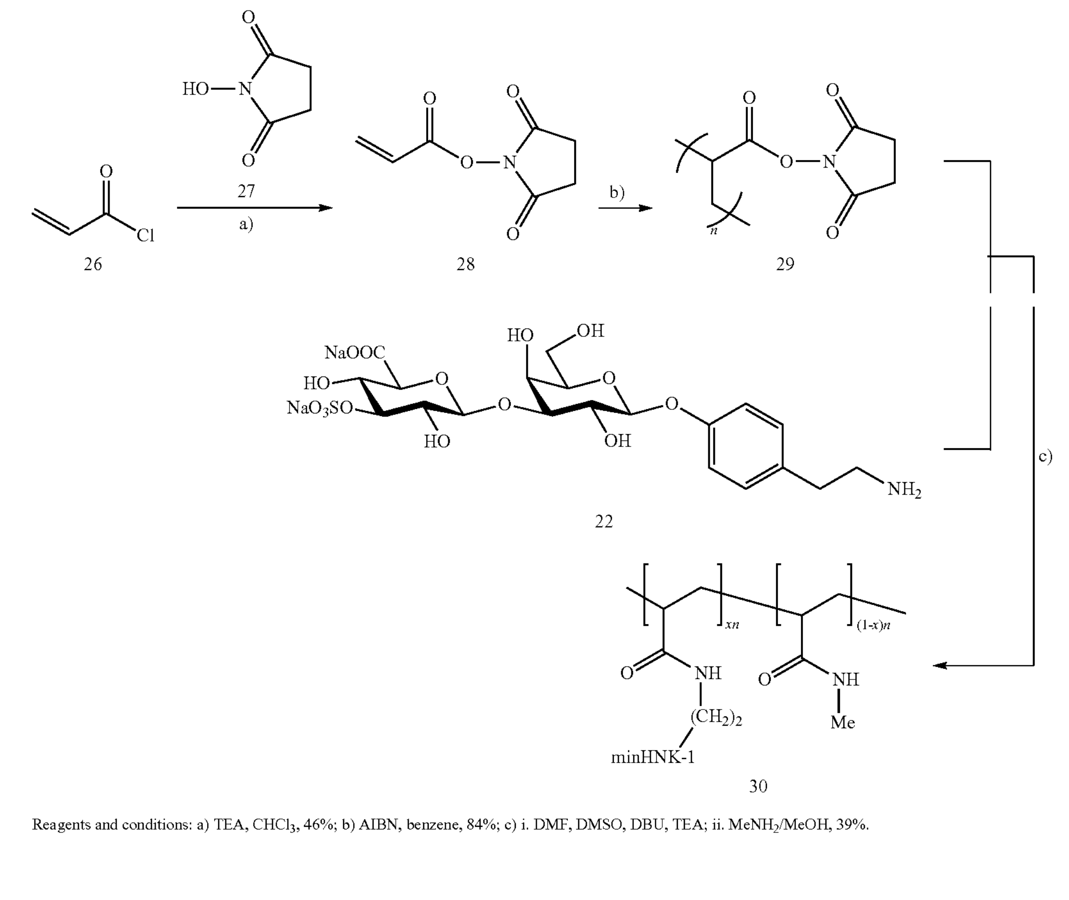

Reagents and conditions: a) TEA, $CHCl_3$, 46%; b) AIBN, benzene, 84%; c) i. DMF, DMSO, DBU, TEA; ii. $MeNH_2$/MeOH, 39%.

2,5-Dioxopyrrolidin-1-Yl Acrylate (28)

To a cooled (ice-bath) solution of N-hydroxysuccinimide (27) (6.41 g, 55.8 mmol) and $NEt_3$ (8.5 mL, 61.0 mmol) in $CHCl_3$ (100 mL) was added acryloyl chloride (26) dropwise under argon. The temperature of the mixture was kept below 12° C. during the addition. After stirring for 2.5 h, the reaction mixture was subsequently washed with ice-water (100 mL), water (100 mL), and brine (100 mL). The organic phase was dried over $Na_2SO_4$, filtered, concentrated in vacuo to 15 mL, and filtered through a pad of celite. The celite was washed with $CHCl_3$ (15 mL), the filtrate was diluted with EtOAc (2 mL) and petroleum ether (11 mL), and stored at −20 ° C. overnight. The formed precipitate was filtered off and dried in vacuo to yield 28 (4.30 g, 25.4 mmol, 46%) as white needles.

Activated Polyacrylate (29)

A solution of 28 (2.10 g, 12.4 mmol) and AIBN (133 mg, 0.81 mmol) in dry benzene (100 mL) was heated at 60 ° C. for 1 d. The formed precipitate was filtered off, washed with dry THF and dried in vacuo to give 29 (1.70 g, 81%) as a white solid. The molecular weight of 29 was determined by gel permeation chromatography (GPC), with Varian polystyrene calibration kit S-M2-10 used as standard. Mn=13.9 kD, Mw=55.3 kD, Mz=127.4 kD, Mp=39.0 kD, Mw/Mn=3.99.

Minimal HNK-1 Polymer (30)

Compound 22 (51 mg, 0.085 mmol), DBU (10.5 mg, 0.183 mmol) and polymer 29 (29 mg) were dissolved in DMF (0.5 mL) and DMSO (1 mL). The reaction mixture was stirred for 18 h. Then, $MeNH_2$ (0.5 mL, 33% solution in MeOH) was added and stirring was continued for 19 h. The mixture was dialyzed subsequently with a 10 kD cut-off membrane in water (1 L), aq. ammonium formiate (40 mM, 1 L), aq. ammonium formiate (60 mM, 2×1 L), and water (2×1 L). Final lyophilization gave minimal HNK-1 polymer 30 (27 mg, 39%) as ammonium salt. According to $^1H$ NMR, the product contained approximately 50% of monomer carbohydrate units linked to the polymer.

Patient Sera

Sera of four patients (three men and one woman) were investigated. They all were tested positive for a monoclonal IgM gammopathy and were diagnosed with anti-MAG neuropathy at the University Hospital of Basel (Basel, Switzerland). Serum anti-MAG antibody titers were determined by an ELISA assay (Bühlmann Laboratories, Schonenbuch, Switzerland). Sera from two patients with a monoclonal IgM gammopathy and negative anti-MAG activity served as control. Use of sera was approved by the ethics committee of the University Hospital of Basel.

Competitive Binding Assay

An anti-MAG ELISA kit (Bühlmann Laboratories, Schonenbuch, Switzerland) was used for the biological evaluation of compounds 1, 2 and 25. The 96 well plates coated with purified MAG from human brain were washed four times with washing buffer (300 μl/well) before adding the carbohydrate ligands in seven different concentrations (0.05-50 mM for the monomers 1 and 2 and 0.05-5,000 nM for the polymer 25), 25 μl/well. The patient sera containing anti-MAG IgM antibodies were added in the appropriate dilutions, 25 μl/well. The measurements were made in duplicate. The plate was covered with a plate sealer and incubated for 2 h at 5° C. The wells were washed four times with wash buffer (300 μl/well) before the enzyme labeled IgM (anti-human IgM antibody conjugated to horseradish peroxidase in a protein-based buffer with preservatives) was added (100 μl/well). The plate was incubated for 2 h at 5° C. After washing the wells (4×300 μl/well), a substrate solution of tetramethylbenzidin (TMB in citrate buffer with hydrogen peroxide) was added (100 μl/well) and the plate incubated for further 30 minutes at 800 rpm and room temperature (rt), protected from daylight. Finally, a stop solution (0.25 M sulfuric acid) was added (100 μl/well) and the degree of colorimetric reaction was determined by absorption measurement at 450 nm with a microplate reader (Spectramax 190, Molecular Devices, California, USA).

The invention claimed is:

1. A method of preparing a HNK-1 polymer comprising a multitude of disaccharide substituents of formula (I):

(I)

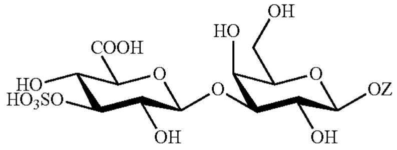

or a salt thereof, wherein:

the polymer backbone is polylysine having a molecular weight of 30,000 D to 70,000 D;

Z is a linker that is phenyl substituted by $-(CH_2)_2NH(C{=}O)(CH_2)_3S-CH_2-(C{=})-$connecting said substituent to lysine sidechains of the polylysine polymer backbone at the C═O function; and 10% to 80% of the lysine sidechains in the polylysine polymer are linked to the disaccharide substituents of formula (I) or a salt thereof and the remaining lysine sidechains in the polylysine polymer are capped with 2,3-dihydroxypropylthioacetyl;

the method comprising:

coupling a sub-stochiometric amount of a compound of formula (Ib):

(Ib)

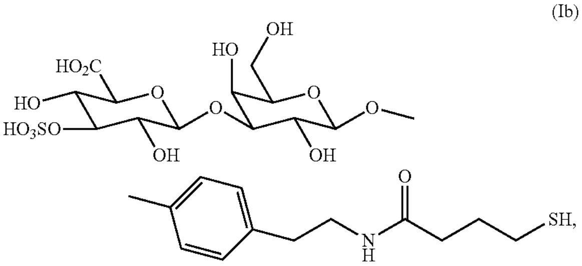

or a salt thereof, with chloroacetamide groups of a chloroacetylated polylysine polymer under conditions sufficient to produce a coupled polylysine polymer; and contacting the coupled polylysine polymer with an excess of thioglycerol under conditions sufficient to substantially cap the remaining chloroacetamide groups and produce the HNK-1 polymer.

2. The method of claim 1, wherein the polylysine polymer is poly-L-lysine polymer.

3. The method of claim 1, further comprising contacting polylysine with chloroacetic anhydride to prepare the chloroacetylated polylysine polymer.

4. The method of claim 1, further comprising contacting a compound of formula:

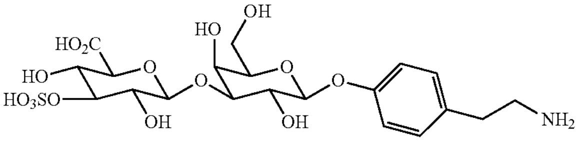

with thiobutyrolactone under conditions sufficient to produce the compound of formula (Ib).

5. The method of claim 1, wherein the compound of formula (Ib) is of the formula:

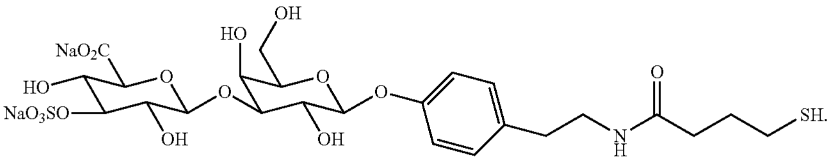

6. The method of claim 1, wherein 30% to 60% of the lysine sidechains in the polylysine polymer are linked to the disaccharide substituents of formula (I) or a salt thereof.

7. The method of claim 1, wherein the method further comprises isolating and purifying the HNK-1 polymer.

8. A method of preparing a HNK-1 linker compound, the method comprising:

contacting a compound of formula (Ic):

(Ic)

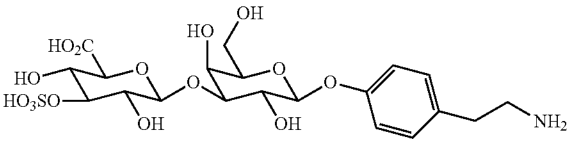

or a salt thereof, with a compound of formula:

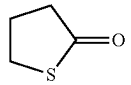

under reaction conditions sufficient to produce a compound of formula (Ib):

(Ib)

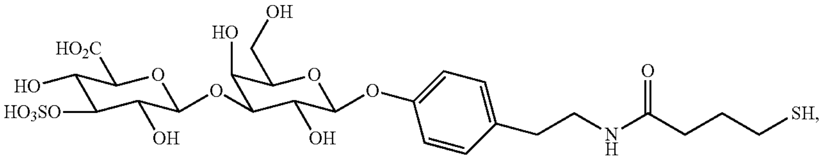

or a salt thereof.

9. The method of claim 8, wherein the compound of formula (Ib) is of the formula:

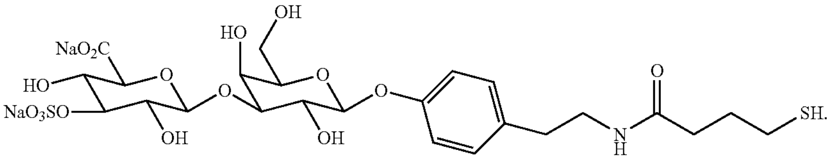

10. The method of claim 8, wherein the compound of formula (Ic) is of the formula:

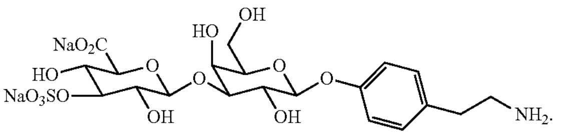

11. The method of claim 9, wherein the contacting step is performed in DMF solvent in the presence of triethylamine.

* * * * *

UNITED STATES PATENT AND TRADEMARK OFFICE

CERTIFICATE OF CORRECTION

PATENT NO. : 11,220,523 B2
APPLICATION NO. : 16/848268
DATED : January 11, 2022
INVENTOR(S) : Ernst et al.

It is certified that error appears in the above-identified patent and that said Letters Patent is hereby corrected as shown below:

On the Title Page

Item (58), in Column 1, under "Field of Classification Search", Line 1, delete "None" and insert -- USPC ........................ 536/123.13 --, therefor.

In the Claims

In Column 42, in Claim 1, Line 21, delete "(C=)" and insert -- (C=O) --, therefor.

Signed and Sealed this
Nineteenth Day of July, 2022

Katherine Kelly Vidal

Katherine Kelly Vidal
*Director of the United States Patent and Trademark Office*